United States Patent [19]

Monteleone et al.

[11] Patent Number: 5,583,264
[45] Date of Patent: Dec. 10, 1996

[54] PARA-C5 ALKY-SUBSTITUTED ETHOXYCYCLOHEXANES, ORGANOLEPTIC USES THEREOF AND PROCESSES FOR PREPARING SAME

[75] Inventors: Michael G. Monteleone, Hazlet; Richard A. Weiss, Pine Brook; Marc D. Evans, South Orange; Marie R. Hanna, Keyport, all of N.J.

[73] Assignee: International Flavors & Fragrances Inc., New York, N.Y.

[21] Appl. No.: 605,446

[22] Filed: Feb. 26, 1996

Related U.S. Application Data

[62] Division of Ser. No. 522,122, Aug. 31, 1995.

[51] Int. Cl.$^6$ .................................................. C07C 41/20
[52] U.S. Cl. ...................... 568/579; 568/319; 568/322; 568/658
[58] Field of Search ........................... 568/579, 319, 568/322, 658

[56]  References Cited

U.S. PATENT DOCUMENTS 2,996,514   8/1961   Schoot et al. .................... 568/658

OTHER PUBLICATIONS

Dutton et al, Canadian J. of Chemistry, vol. 31, pp. 1138–1142 (1953).
Zavgorodnii, Chem Abst, vol 71, #3088M (1969).

*Primary Examiner*—James H. Reamer
*Attorney, Agent, or Firm*—Arthur L. Liberman

[57] ABSTRACT

Described are compounds defined according to the structure:

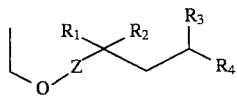

wherein Z represents para cyclohexylene or para phenylene and wherein $R_1$, $R_2$ and $R_3$ are the same or different methyl or hydrogen; and wherein $R_4$ represents hydrogen, methyl or ethyl with the proviso that the sum of the carbon atoms in $R_1$, $R_2$, $R_3$ and $R_4$ is 2. Also described are para-$C_5$ alkyl-substituted ethoxycyclohexanes defined according to the structure:

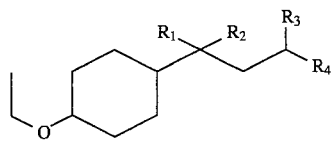

wherein $R_1$, $R_2$ and $R_3$ represent the same or different methyl or hydrogen; and wherein $R_4$ represents hydrogen, methyl or ethyl with the proviso that the sum of the carbon atoms in $R_1$, $R_2$, $R_3$ and $R_4$ is 2 and uses thereof in augmenting or enhancing the aroma of perfume compositions, colognes and perfumed articles including but not limited to solid or liquid anionic, cationic, nonionic or zwitterionic detergents, fabric softener compositions, fabric softener articles and hair preparations; as well as processes for preparing said para-$C_5$ alkyl-substituted ethoxycyclohexanes.

2 Claims, 18 Drawing Sheets

CAPILLARY GC PROFILE
FOR EXAMPLE I(A)

FIG.3 CAPILLARY GC PROFILE FOR EXAMPLE I(B)

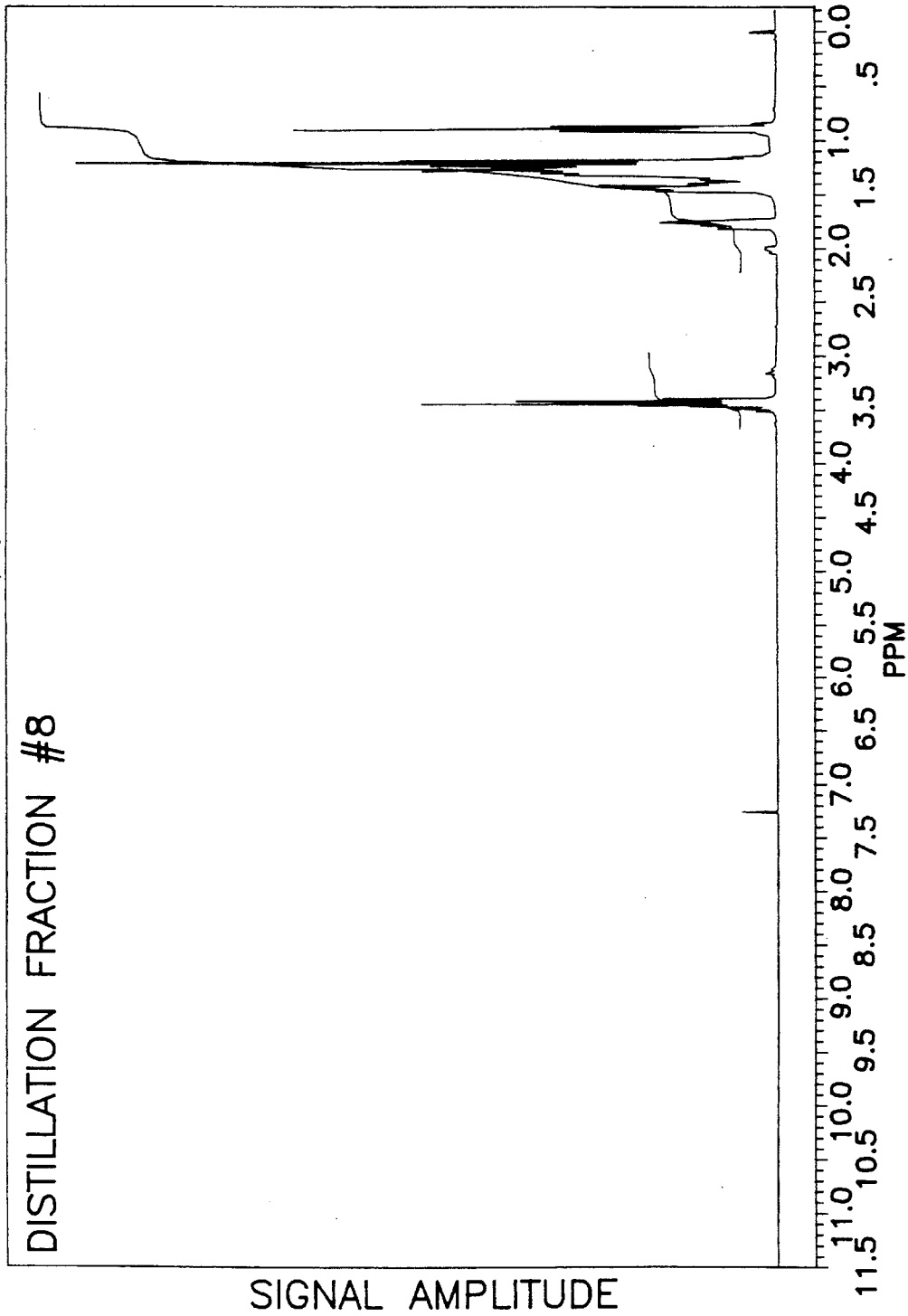

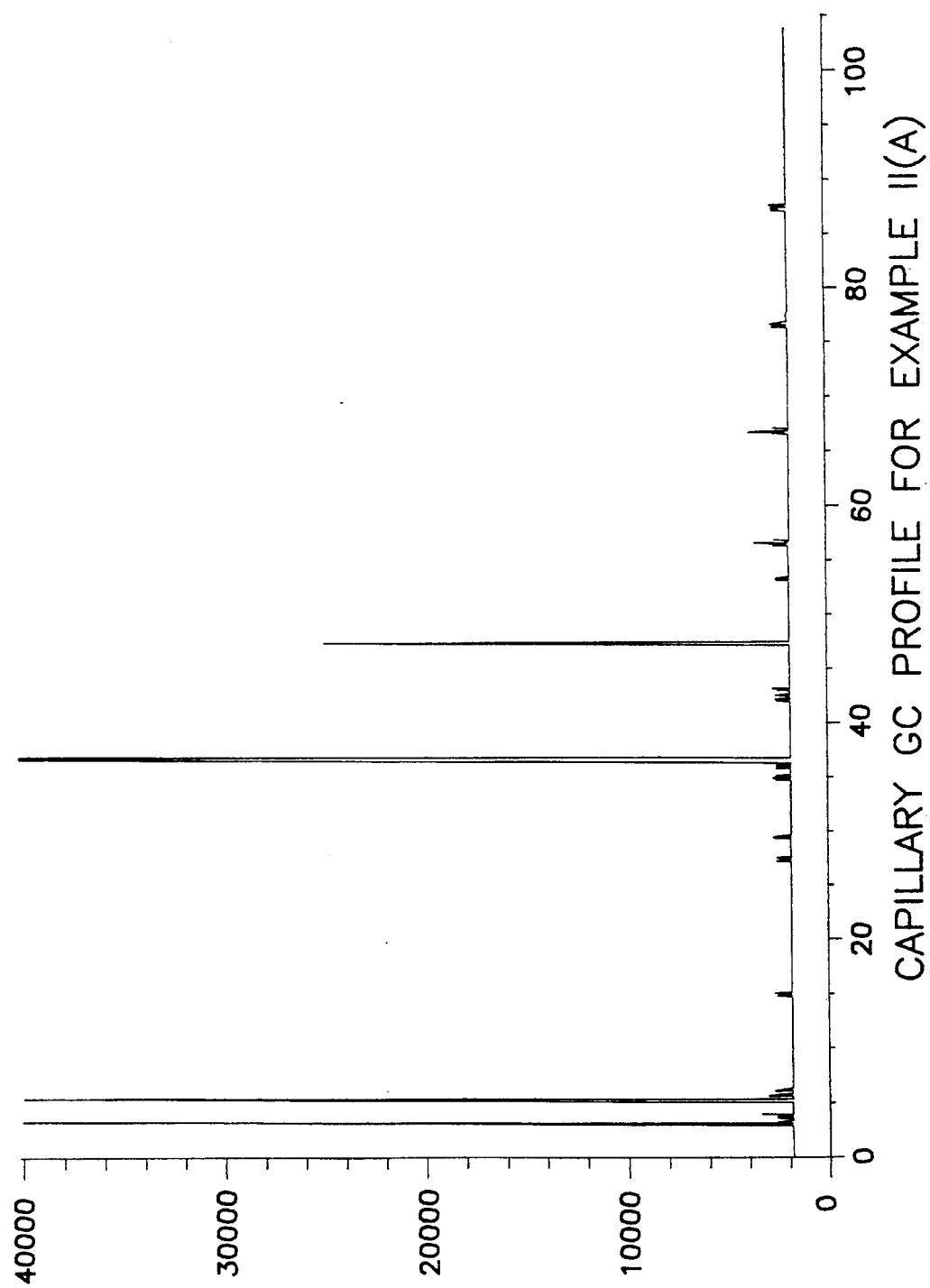

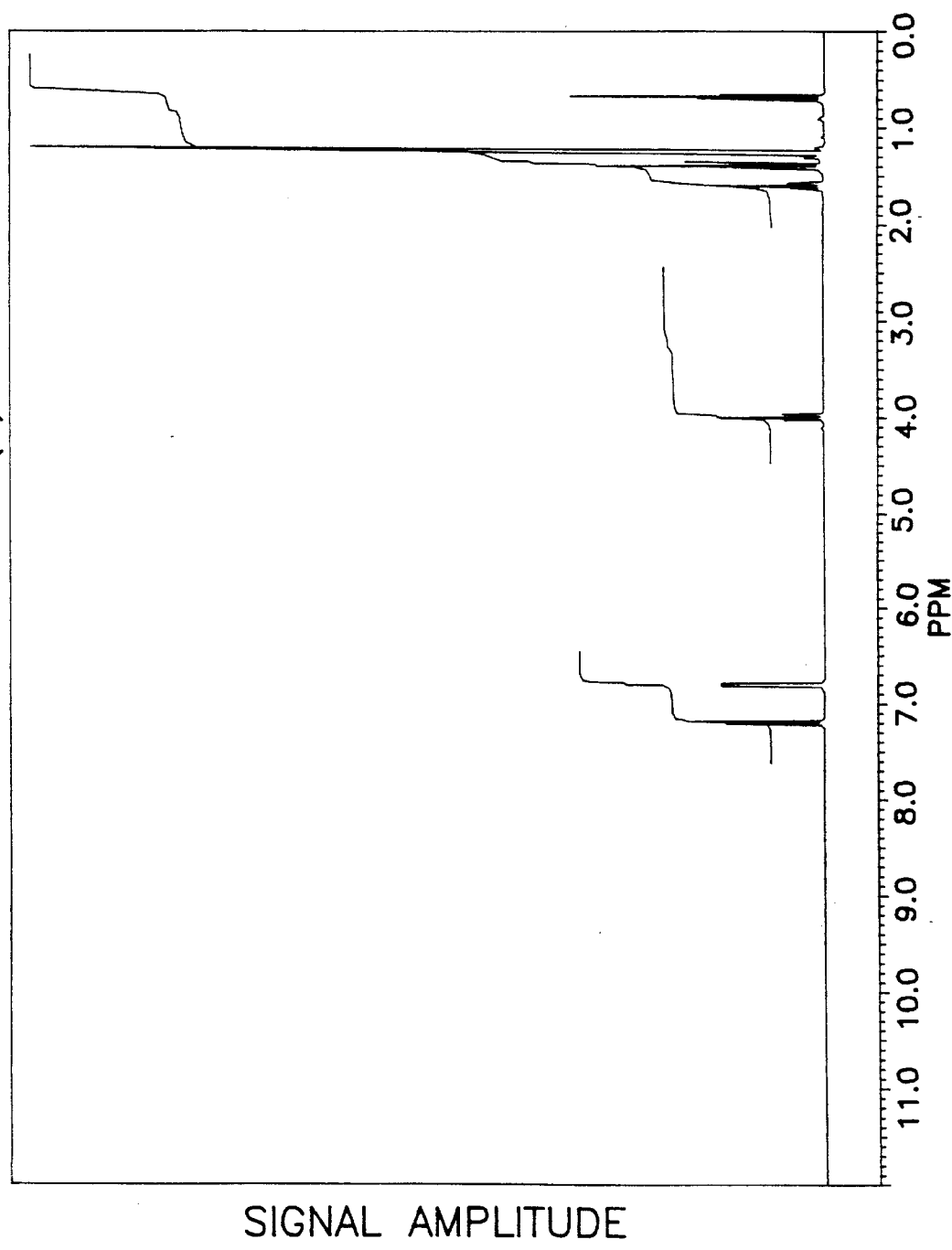

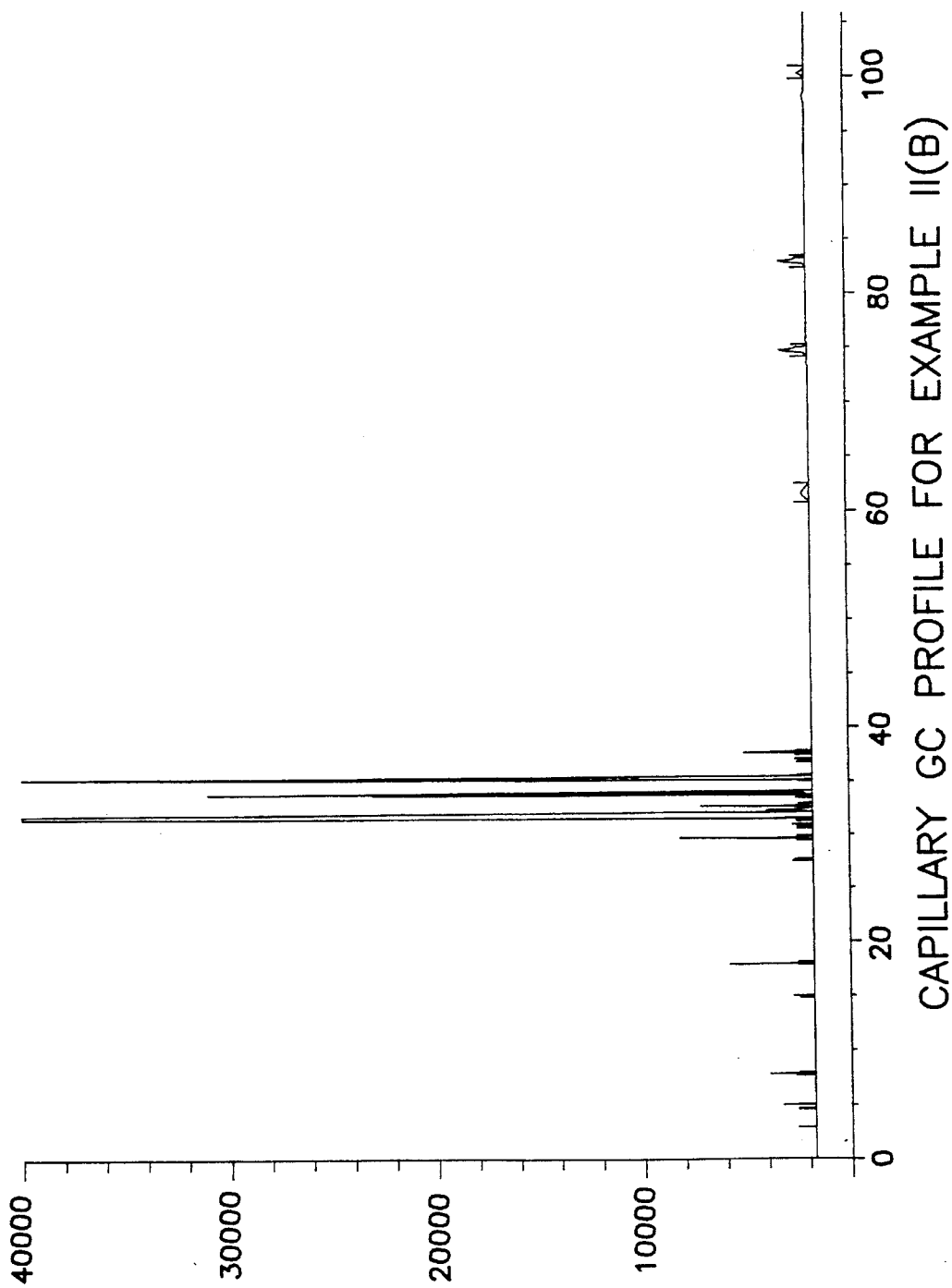
FIG.8 CAPILLARY GC PROFILE FOR EXAMPLE II(B)

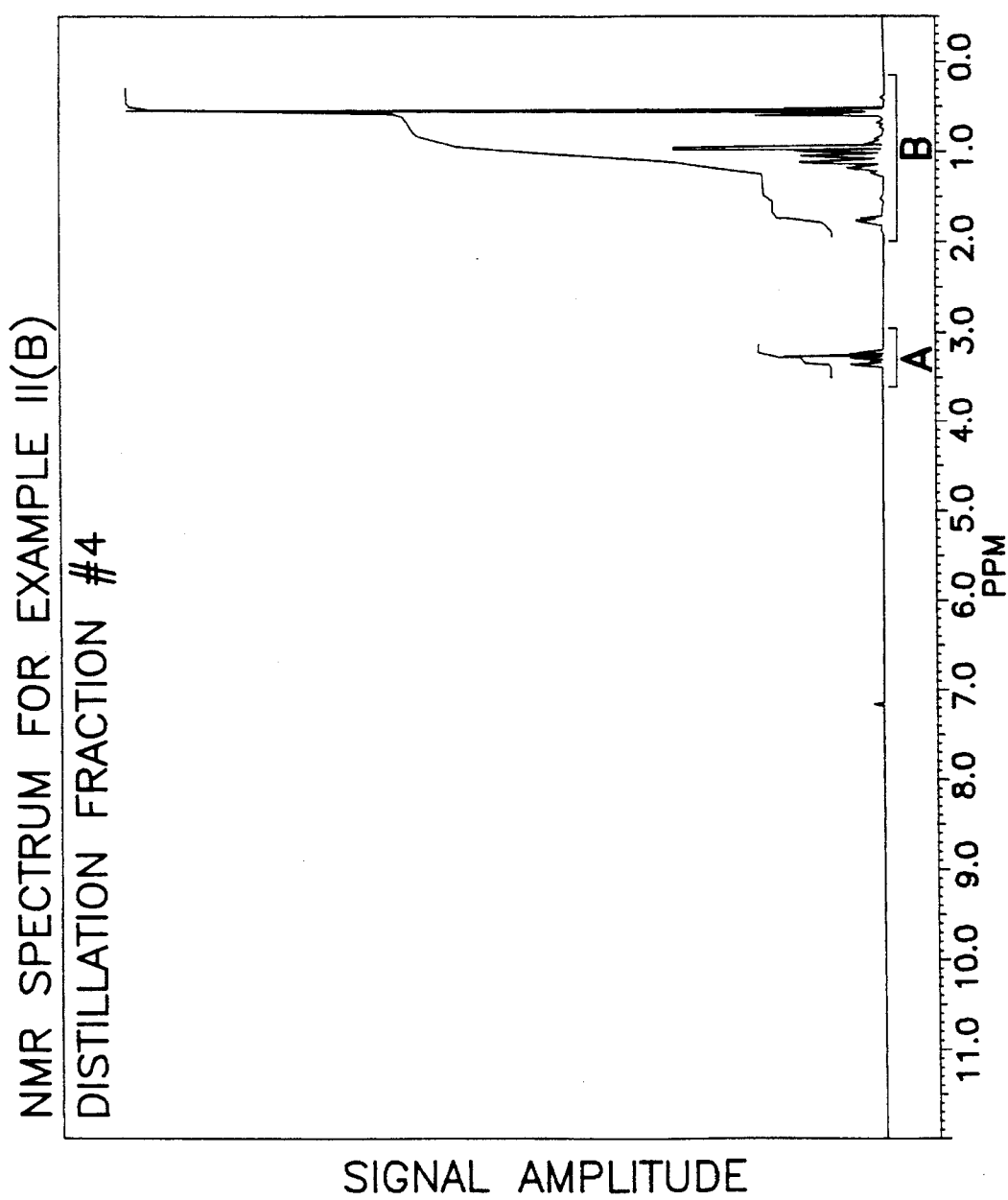

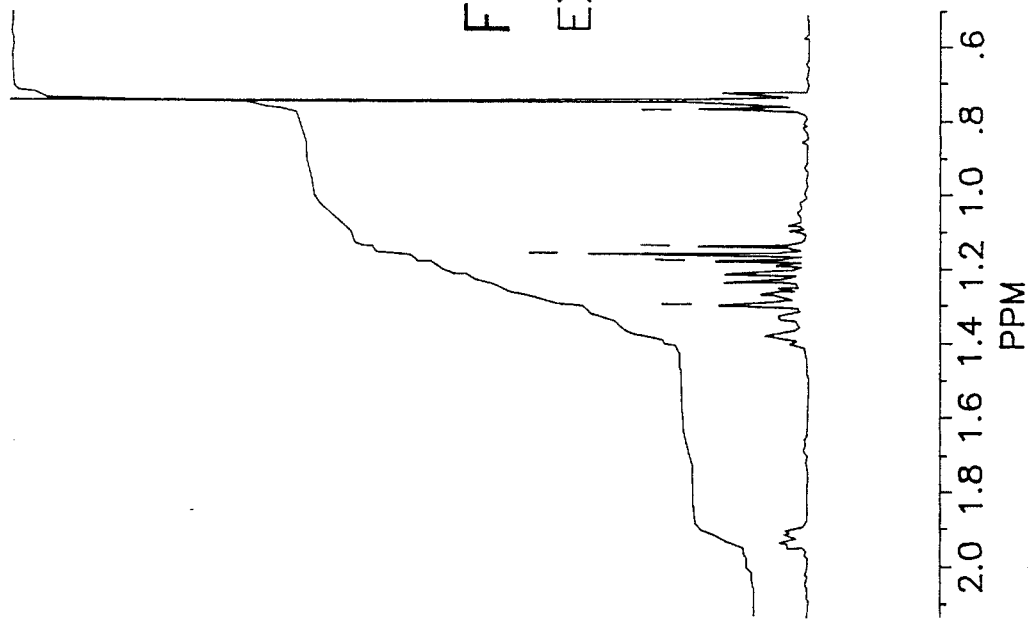
FIG.9(B) EXAMPLE II(B)
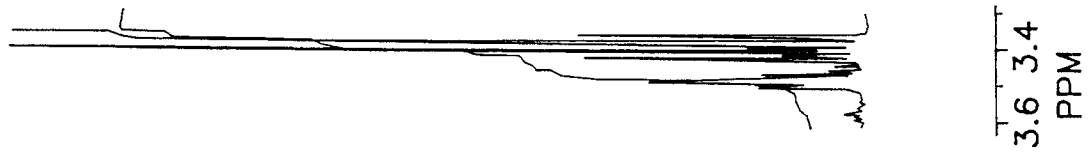
FIG.9(A) EXAMPLE II(B)

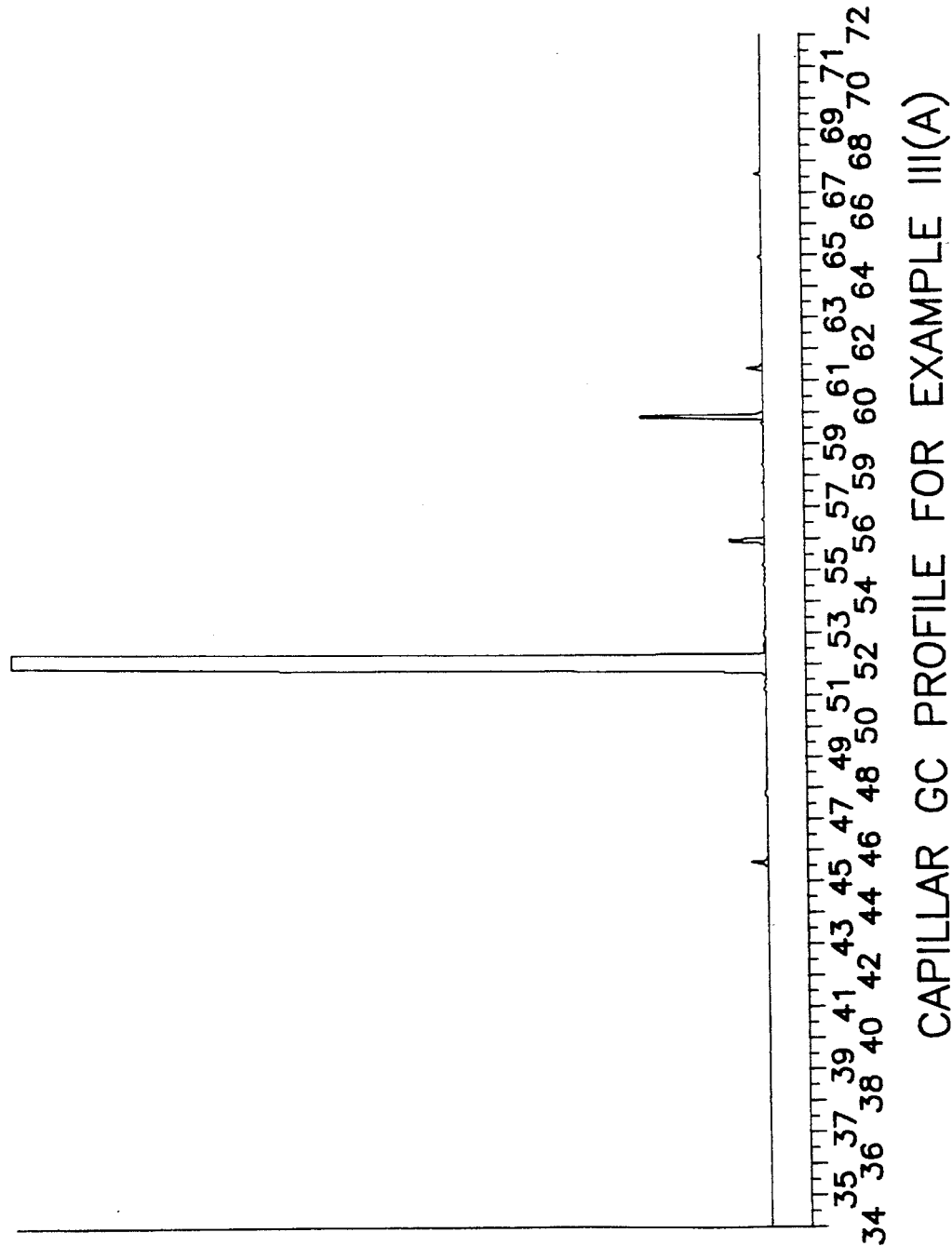

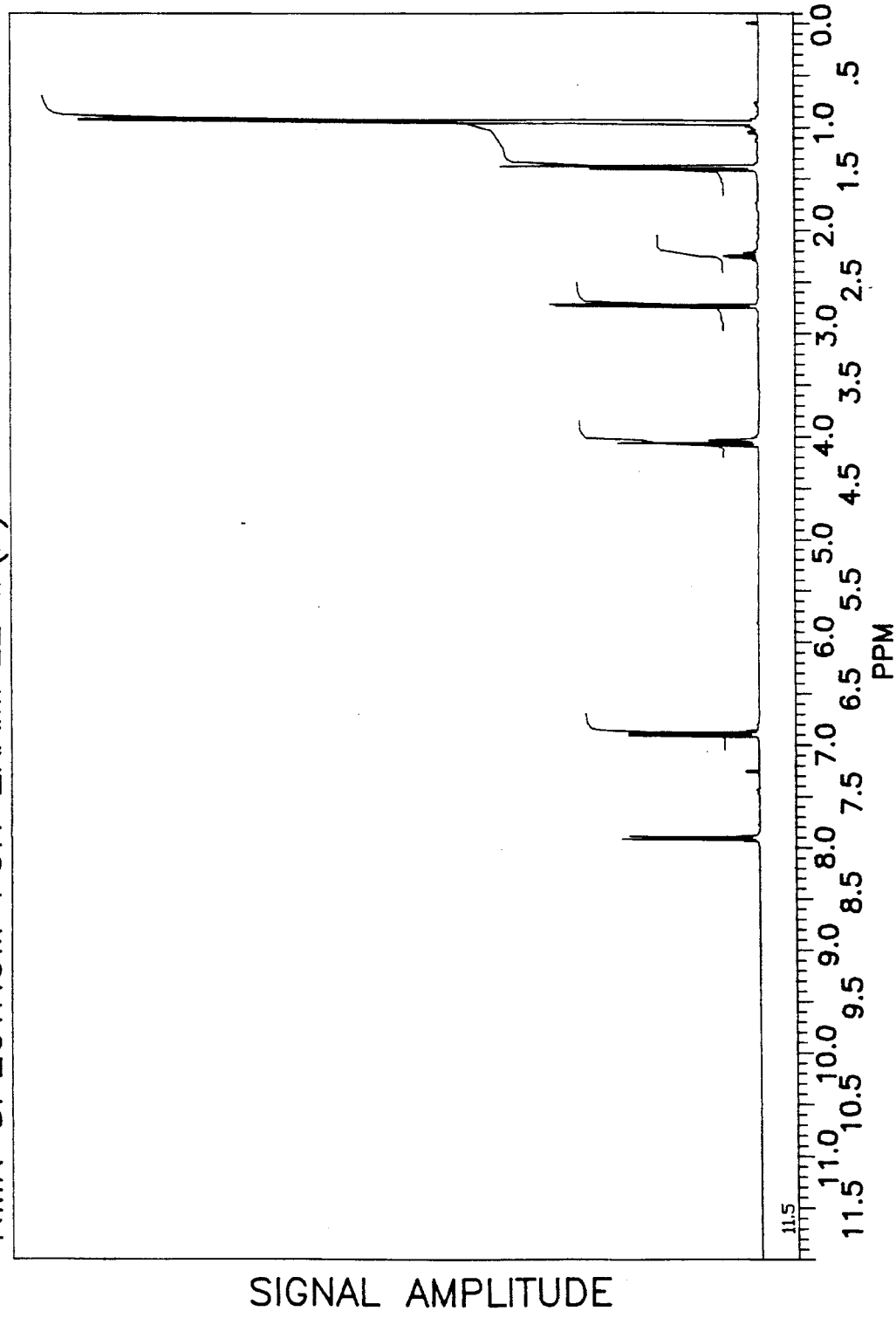

CAPILLARY GC PROFILE FOR EXAMPLE III(B)

PARA-C5 ALKY-SUBSTITUTED ETHOXYCYCLOHEXANES, ORGANOLEPTIC USES THEREOF AND PROCESSES FOR PREPARING SAME

This is a divisional of application Ser. No. 08/522,122 filed on Aug. 31, 1995.

BACKGROUND OF THE INVENTION

The instant invention relates to para-$C_5$ alkyl-substituted ethoxycyclohexanes defined according to the structure:

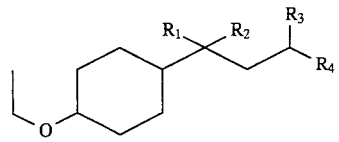

wherein $R_1$, $R_2$ and $R_3$ represent the same or different methyl or hydrogen; and wherein $R_4$ represents hydrogen, methyl or ethyl with the proviso that the sum of the carbon atoms in $R_1$, $R_2$, $R_3$ and $R_4$ is 2 and uses of same in augmenting or enhancing the aroma of perfume compositions, perfumed articles and colognes.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting, intense, substantive green, fresh cut grass-like, citrus, privet hedge (*Ligustrum vulgare*)-like, woody, floral, muguet, rose petal, balsamic and tomato leaf aromas with green, ozoney, woody, floral, muguet, rose, powdery, robusta coffee, dark cocoa, fruity, fatty-oily and tomato leaf topnotes and linden blossom, cucumber and melon-like undertones are highly desirable in several types of perfume compositions, perfumed articles and colognes (e.g., fruity and floral fragrances).

Perfume uses of ethoxycycloalkyl derivatives are well known in the literature. Thus, Arctander "*Perfume and Flavor Chemicals (Aroma Chemicals)*", Volume I, published in 1969 by the author at Monograph No. 713 discloses the compound having the structure:

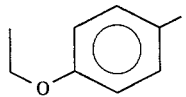

for use in perfumery. Arctander discloses that the compound having the structure:

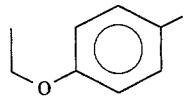

has a powerful, pungent-floral, deep-sweet, warm odor suggestive of ylang-ylang, pandanus and other exotic flowers. Arctander indicates that this compound is useful in perfume compositions of the heavy-floral type, in artificial ylang-ylang and in various types of soap perfumes and in general as a floralizer with considerable power. Arctander further states that the compound having the structure:

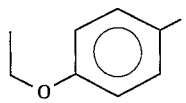

has a "peculiar nut-like, or earthy undertone". *Bielstein*, Volume E II 6, 488, H6, System 530a, 522–523 (abstract of Le Brazidec, *Bull. Soc. Chim.* France[4], 31, 263) discloses that the compound having the structure:

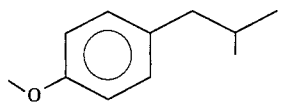

has an anisic aroma. The synthesis of this compound is disclosed by Le Brazidec and is further disclosed by Dutton, et al, *Canadian Journal of Chemistry*, 31 (1953), 1138, 1140. The structure:

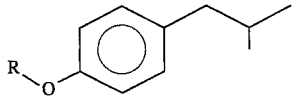

wherein R is methyl is shown by *Bielstein*, Volume E IV 6 at page 3288 and is also disclosed at *Chemical Abstracts*, Volume 47, No. 2716h (abstract of J. Elisha Mitchell Sci. Soc., Volume 66, 171–4 (1950)). The compound having the structure:

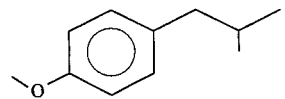

is also disclosed in Schoot, et al, U.S. Pat. No. 2,996,514.

The compounds having the structures:

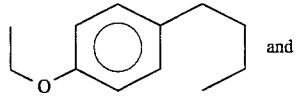 and

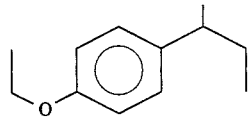

are indicated to be prepared by *Chemical Abstracts*, Volume 73, 1970, 66192c. The preparation of the compound having the structure:

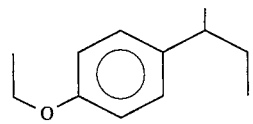

is also shown to be prepared by *Bielstein*, Volume E IV 6 at page 3280, *Chemical Abstracts*, 1961, 13386d (Zavgorodnii II) and *Chemical Abstracts*, Volume 49 (1955), No. 8848z (Zavgorodnii I).

Furthermore, the compound having the structure:

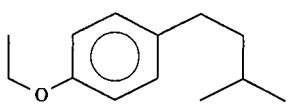

is shown to be prepared by Zavgorodnii III at *Chemical Abstracts*, Volume 71 (1969), No. 3088m. the compound having the structure:

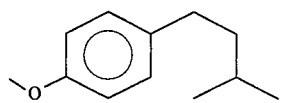

is shown to be prepared using the compound having the structure:

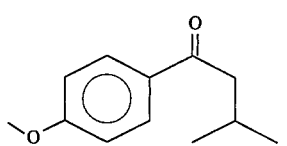

as a starting material according to the reaction:

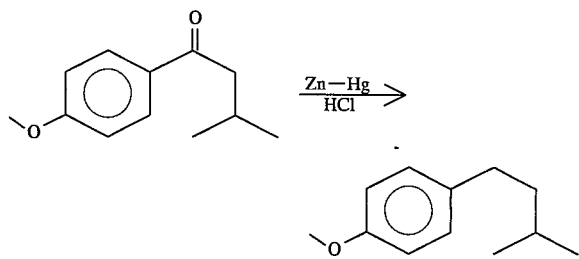

by *Bielstein*, E III 6, H6, 548. The compound having the structure:

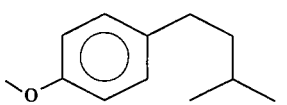

is shown to be prepared using as a starting material the compound having the structure:

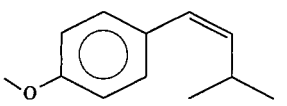

according to the reaction:

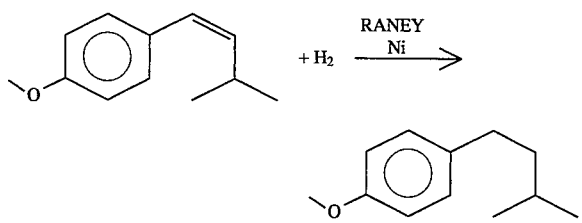

by *Bielstein*, E IV 6, page 3378 and by Dutton, et al, *Canadian Journal of Chemistry*, 31 (1953), pages 1138, 1142.

The compound having the structure:

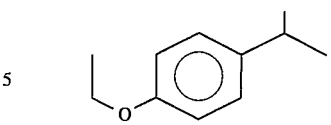

is shown to be prepared by *Bielstein*, E III 6, H6, 505–6, System No. 530, abstract of Ipatieff, et al, *Journal of American Soc.*, 60 (1938), 1161 and Bert, *Bull. Soc. Chim.*, 37, 1252–70 (1925).

Copending Application for patent U.S. Ser. No. 08/428,420 filed on Apr. 25, 1995, Monteleone, et al describes 1-oxo-substituted and unsubstituted isobutyl-4-ethoxy-benzenes and mixtures thereof with bicyclopentadiene derivatives for use in perfumery and further discloses methods for preparing same. Said Application for patent U.S. Ser. No. 08/428,420 is a Divisional of Application for patent U.S. Ser. No. 08/299,966 filed on Sep. 2, 1994 now U.S. Pat. No. 5,462,923 having the same title. Both Ser. Nos. 08/299,966 and 08/428,420 disclose the compounds having the structures:

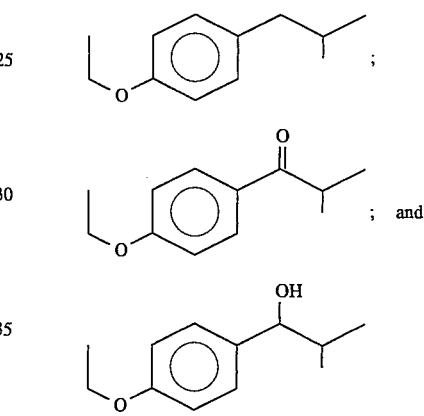

for use in perfumery and further disclose that these compounds have "long-lasting, intense, substantive green, woody, privet hedge (*Ligustrum vulgare*)-like, floral, lilac, ozoney, fennel and anisic aromas with fruity, fresh green, ozoney, fresh air, "ocean breeze" and anisic topnotes".

Alkylcyclohexanols are known to be useful in the field of perfumery. Thus, "VERTENEX®" is an article of commerce marketed by International Flavors & Fragrances Inc., said "VERTENEX®" having the structure:

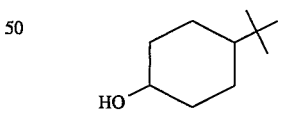

Furthermore, "VERTENEX® HIGH CIS" is also an article of commerce marketed by International Flavors & Fragrances Inc., which has the structure:

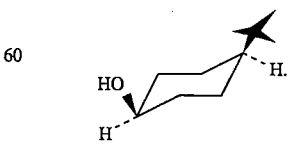

Furthermore, "ORIVONE", also an article of commerce marketed by International Flavors & Fragrances Inc., has the structure:

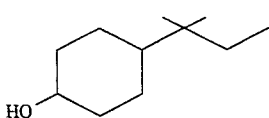

Para alkylcyclohexylalkyl ethers are known in the prior art. Thus, Eliel, et al, *Chemical Abstracts,* Volume 63, 1965, 3011g (abstract of *J. Org. Chem.* 30(3), pages 848–854) discloses the compound having the structure:

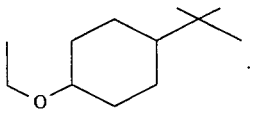

Faillebin, *Beilstein,* Volume E II 6 at H7, No. 2, discloses the compound having the structure:

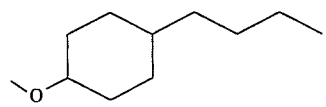

(abstract of Faillebin, *ANN. CHIM.* 4, 156–82, 410–96 (1925)). Hiromu, et al, *Chemical Abstracts,* Volume 108, 1988 at monograph No. 108:62302g, discloses the compound having the structure:

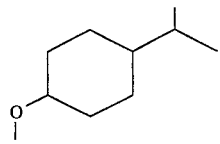

as being a component of an essential oil obtained from the root of *Glycyrrhiza glabra* (abstract of *Nippon Nogei Kagaku Kashi* 1987, 61(9), pages 1119–21 (Japan)). However, the aroma of this material is not disclosed nor is it indicated that the compound having the structure:

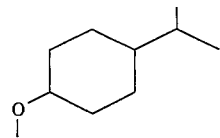

contributes any aroma to the essential oil named.

Thus, nothing in the prior art discloses the unexpected, unobvious and advantageous organoleptic properties of the para-$C_5$ alkyl-substituted ethoxycyclohexanes of our invention.

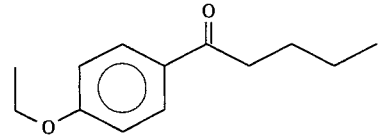

Figure 2:
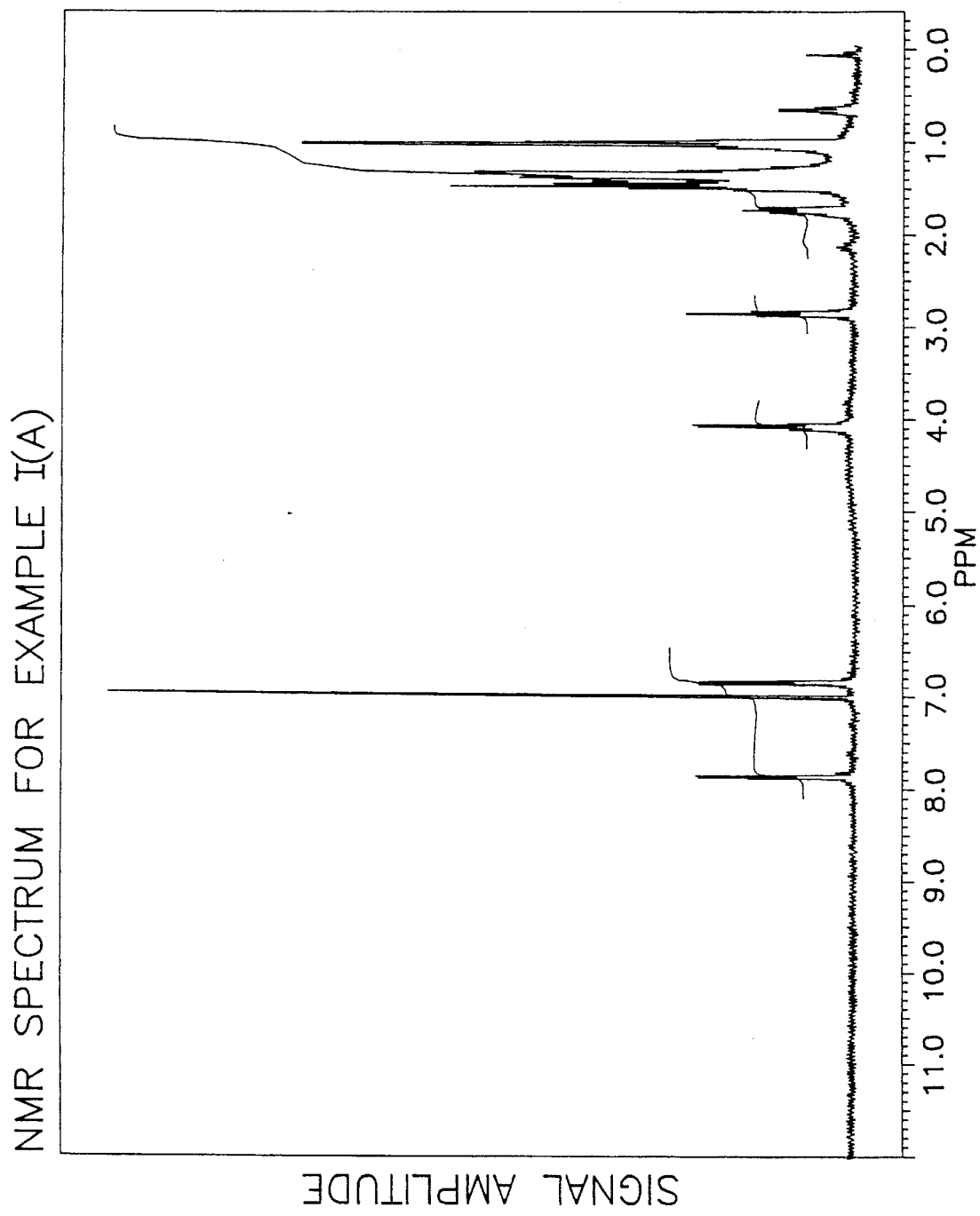

FIG. 2 is the NMR spectrum for the compound having the structure:

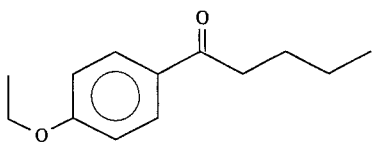

prepared according to Example I(A)

Figure 3:
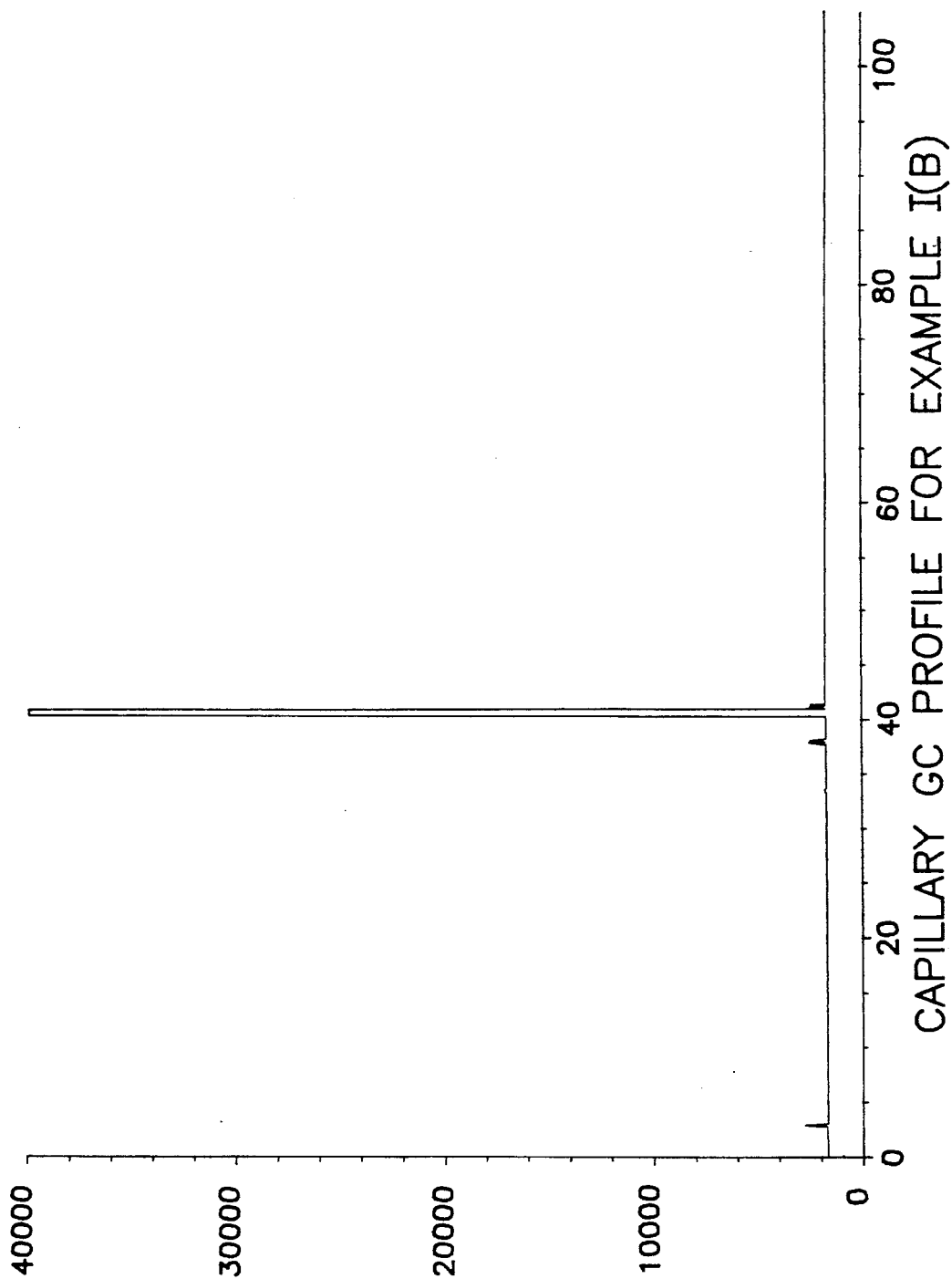

FIG. 3 is the capillary GC profile for the reaction product of Example I(B) containing the compound having the structure:

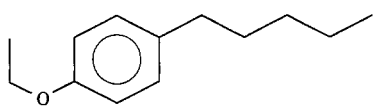

Figure 4:
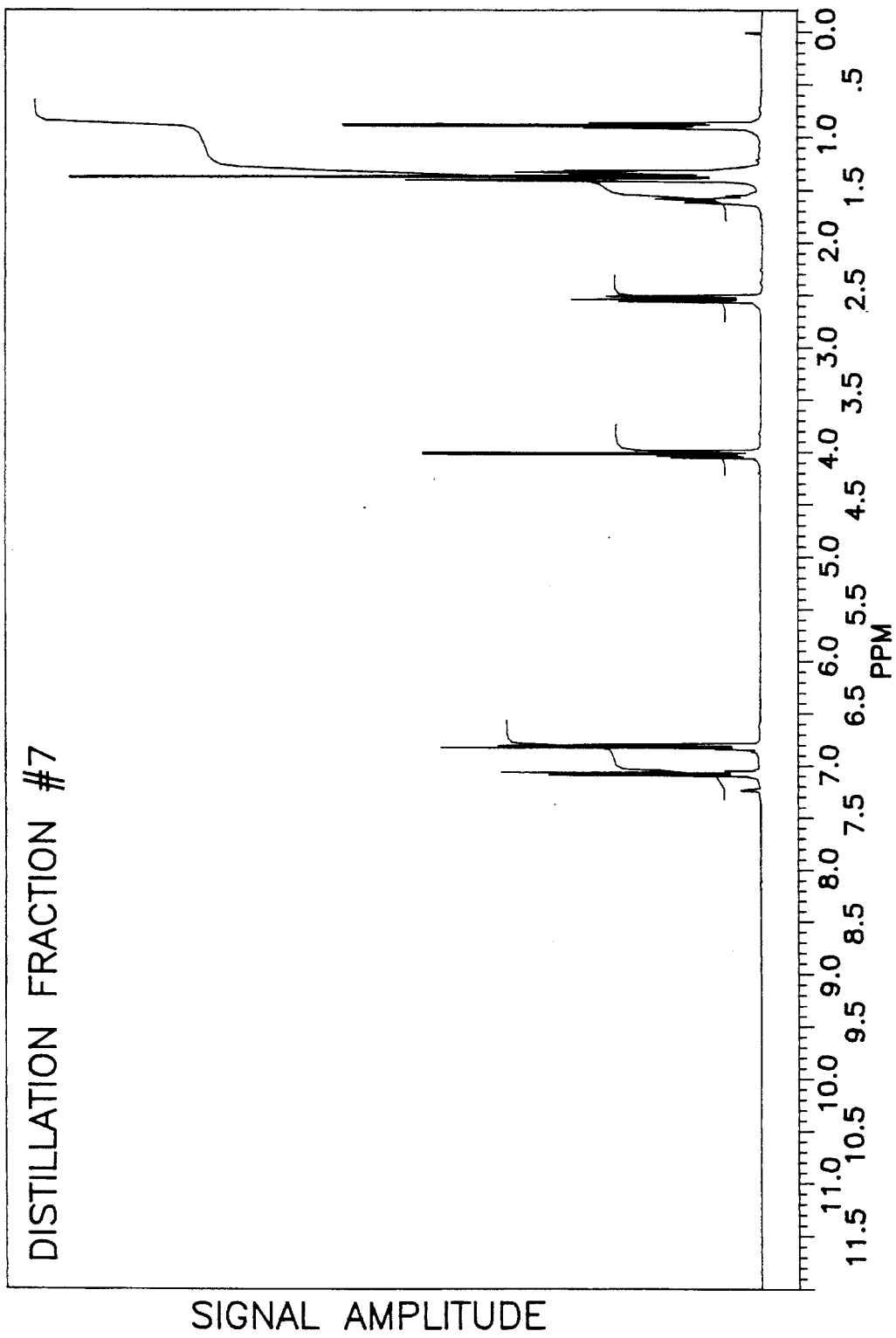

FIG. 4 is the NMR spectrum for distillation fraction No. 7 of the distillation of the reaction product of Example I(B) for the compound having the structure:

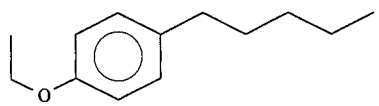

Figure 5:
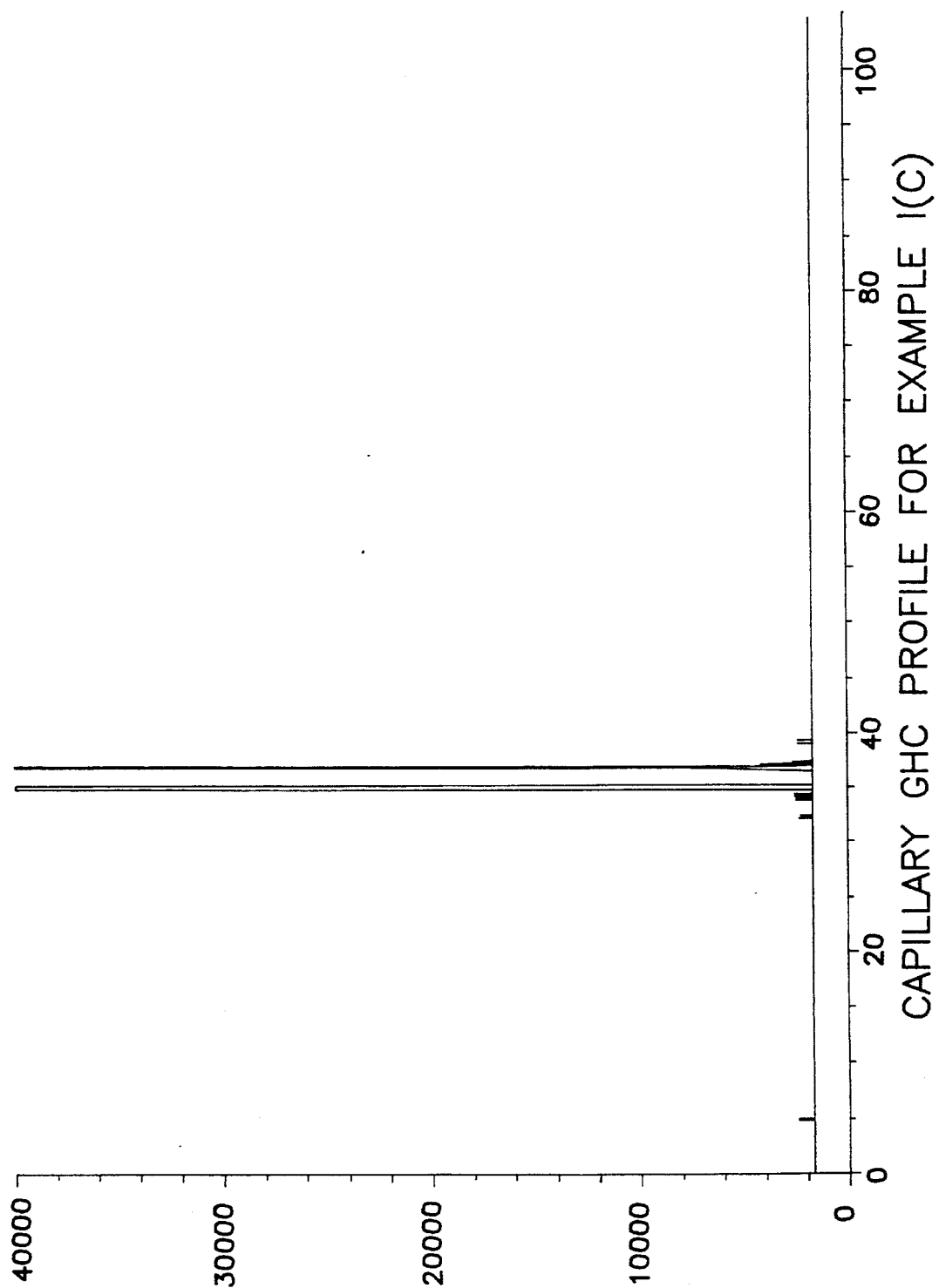

FIG. 5 is the capillary GC profile for the reaction product of Example I(C) containing the compounds having the structures:

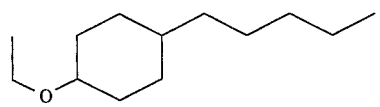

and

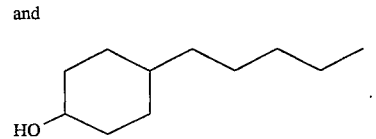

FIG. 6 is the NMR spectrum for distillation fraction No. 8 of the distillation of the reaction product of Example I(C) for the compound having the structure:

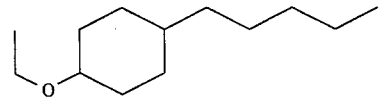

FIG. 7(A) is the capillary GC profile for the crude reaction product of Example II(A) containing the compound having the structure:

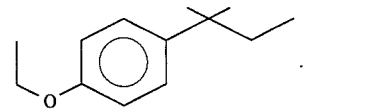

FIG. 7(B) is the NMR spectrum for the compound having the structure:

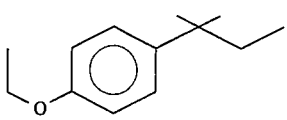

prepared according to Example II(A).

FIG. 8 is the capillary GC profile for the reaction product of Example II(B) containing the compounds having the structures:

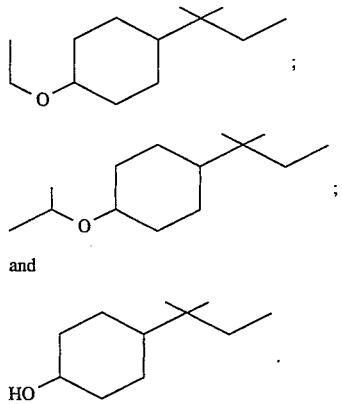

and

FIG. 9 is the NMR spectrum for distillation fraction No. 4 of the distillation of the reaction product of Example II(B) for the compound having the structure:

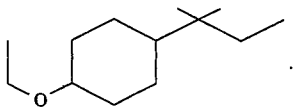

FIG. 9(A) is an enlargement of section "A" of the NMR spectrum of FIG. 9.

FIG. 9(B) is an enlargement of section "B" of the NMR spectrum of FIG. 9.

FIG. 10 is the capillary GC profile for the reaction product of Example III(A) containing the compound having the structure:

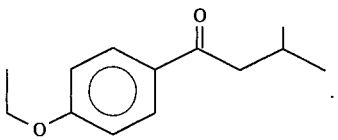

FIG. 11 is the NMR spectrum for the compound having the structure:

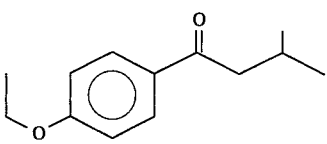

prepared according to Example III(A).

Figure 12:
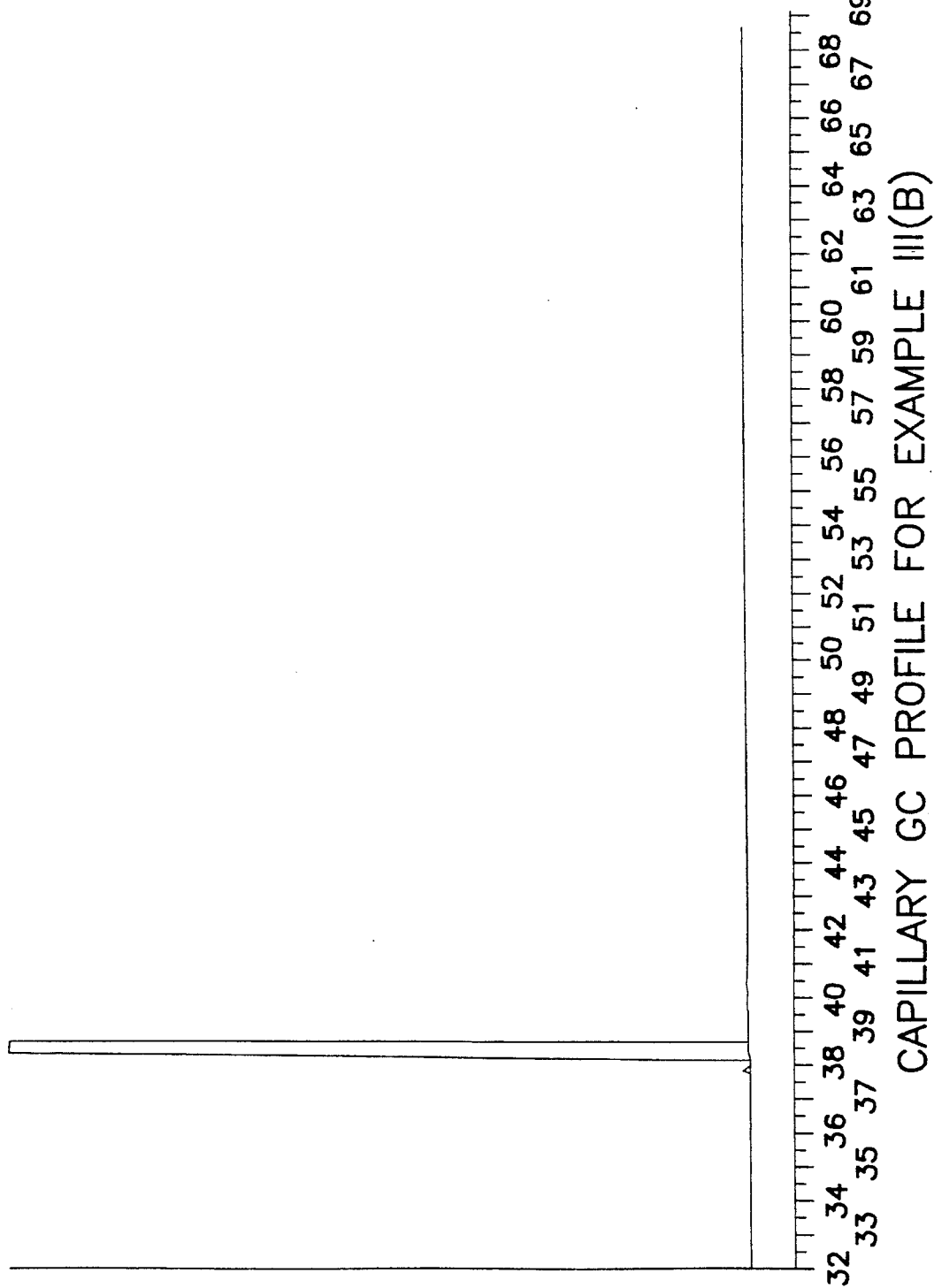

FIG. 12 is the capillary GC profile for the product produced according to Example III(B) containing the compound having the structure:

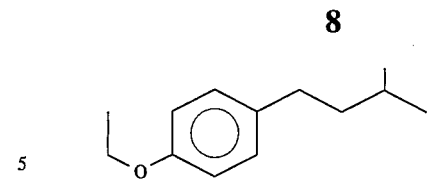

Figure 13:
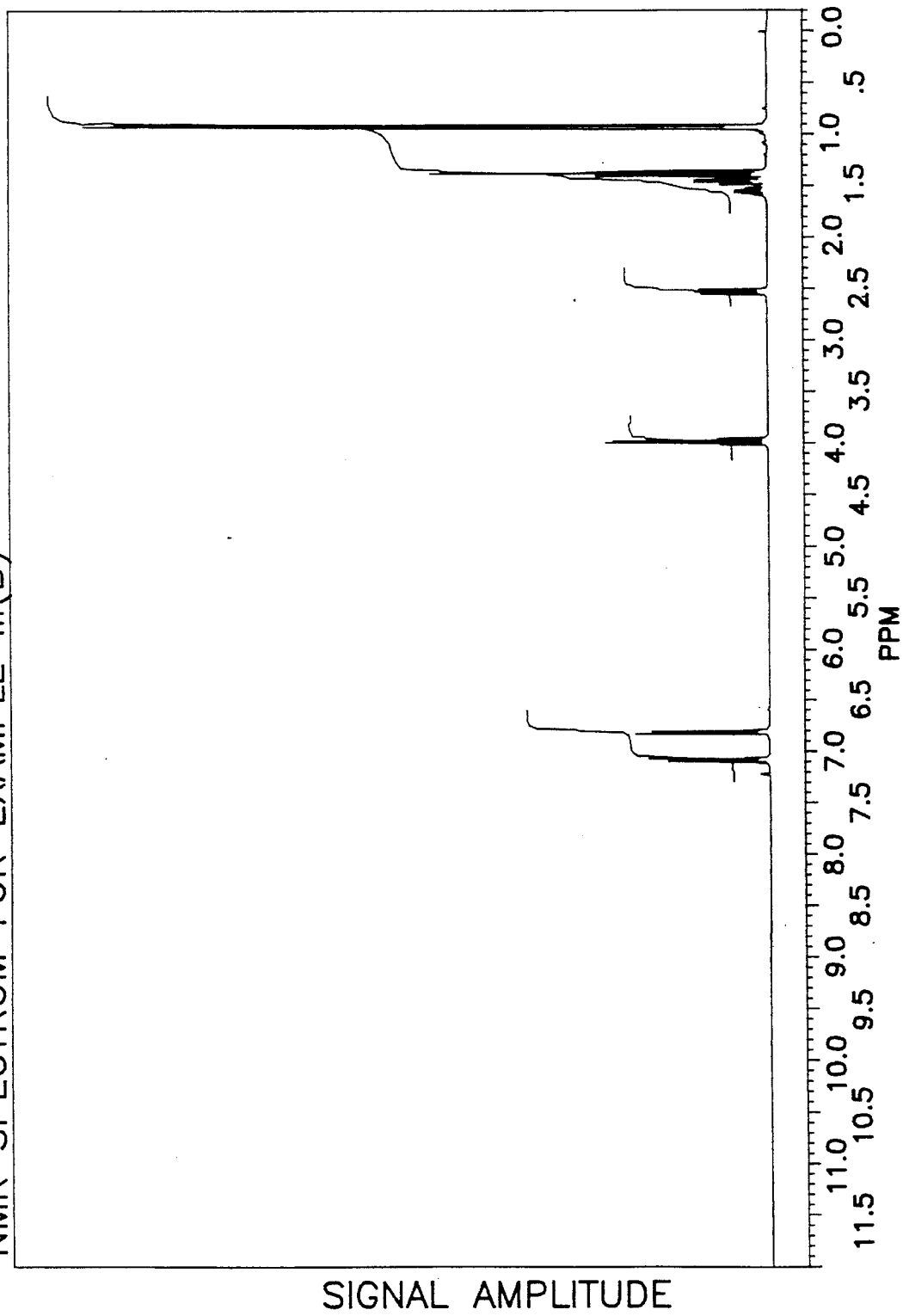

FIG. 13 is the NMR spectrum for the compound having the structure:

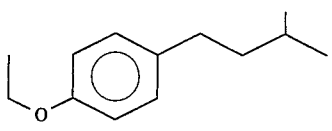

prepared according to Example III(B).

Figure 14:
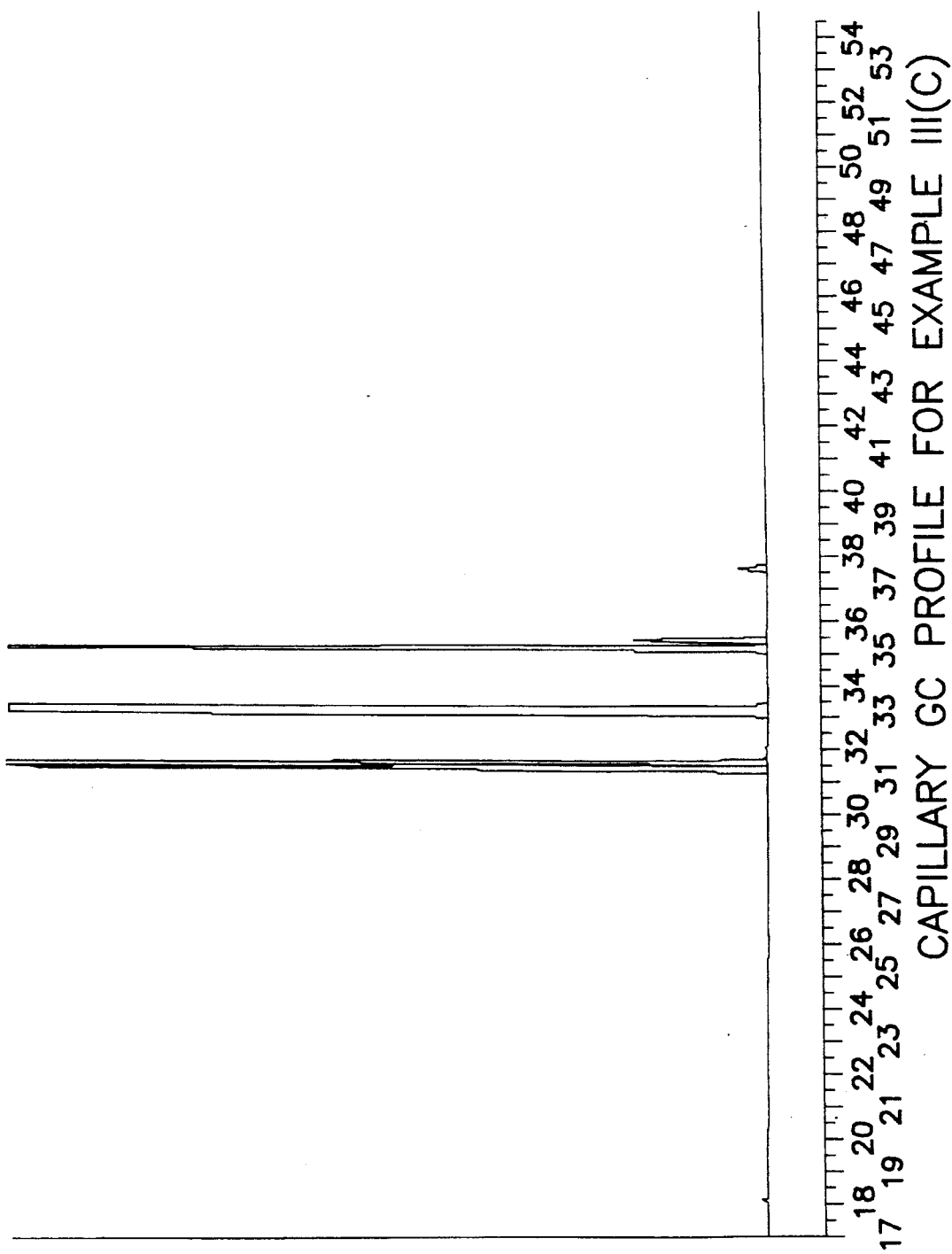

FIG. 14 is the capillary GC spectrum for the reaction product of Example III(C) containing the compounds having the structures:

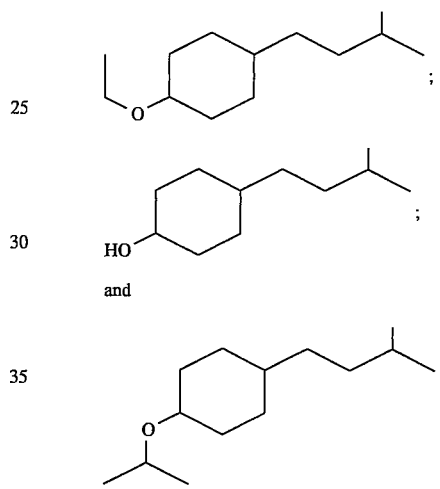

and

Figure 15:
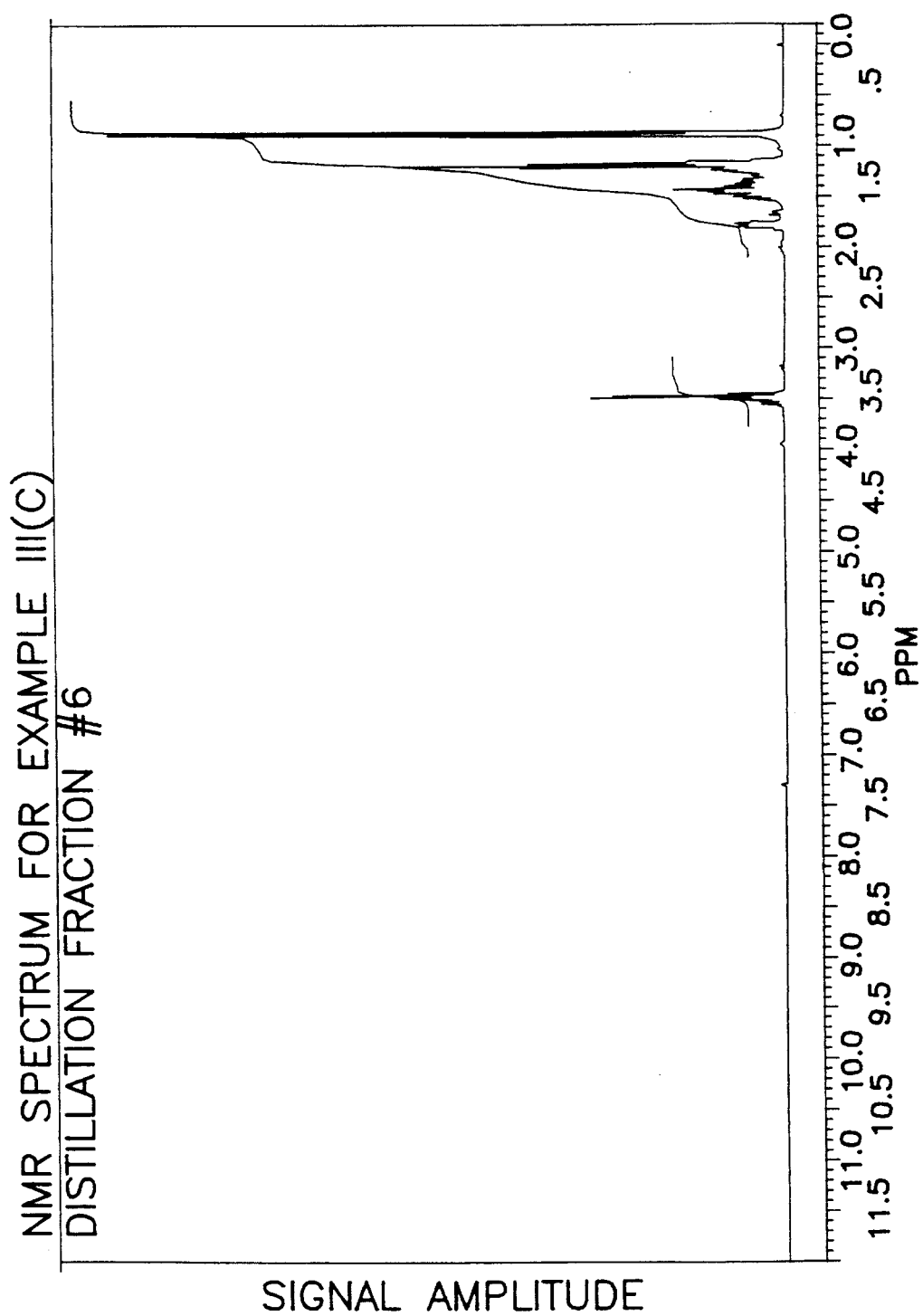

FIG. 15 is the NMR spectrum of distillation fraction No. 6 of the distillation of the reaction product of Example III(C) for the compound having the structure:

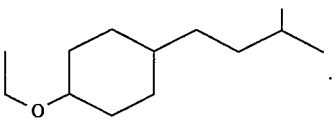

Figure 16:
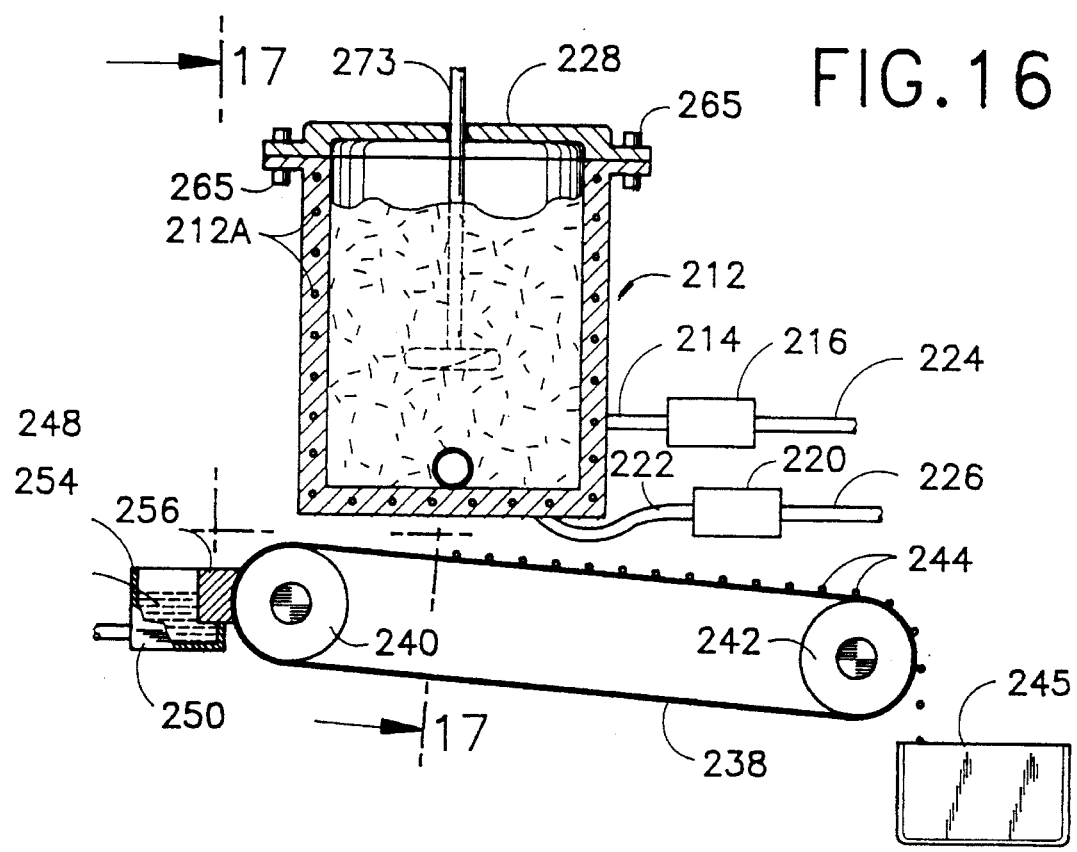

FIG. 16 is a partial side elevation view and partial sectional view of an apparatus for forming polymer pellets containing at least one of the para-$C_5$ alkyl-substituted ethoxycyclohexanes of our invention.

Figure 17:
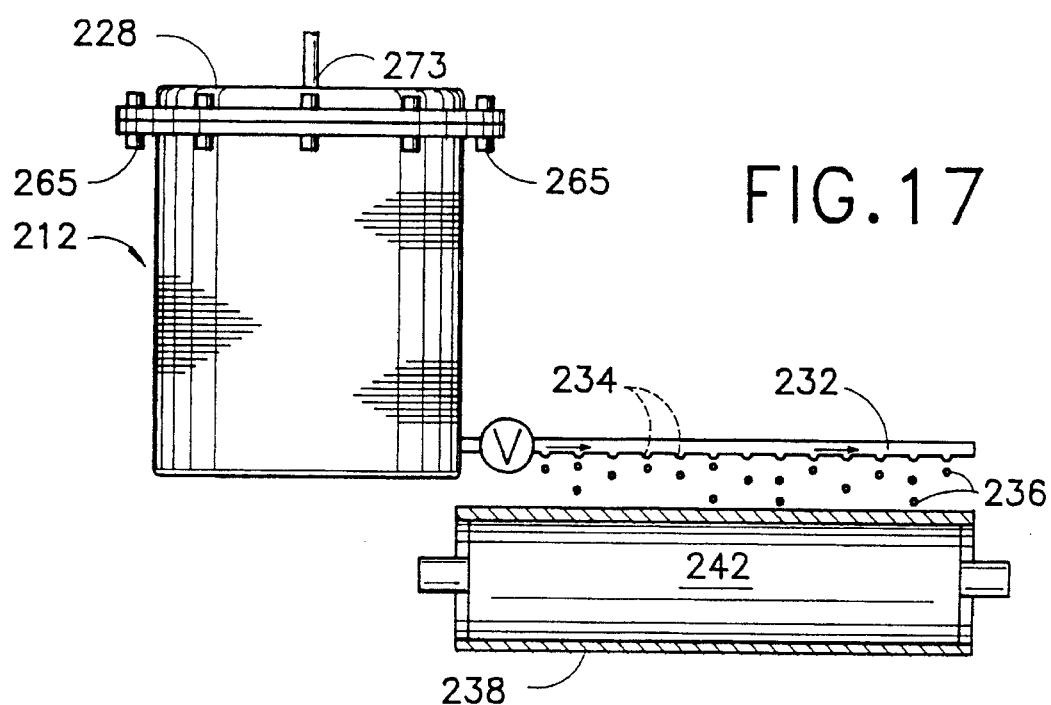

FIG. 17 is a section taken along the line 17—17 of FIG. 16.

DETAILED DESCRIPTION OF THE DRAWINGS

Figure 1:
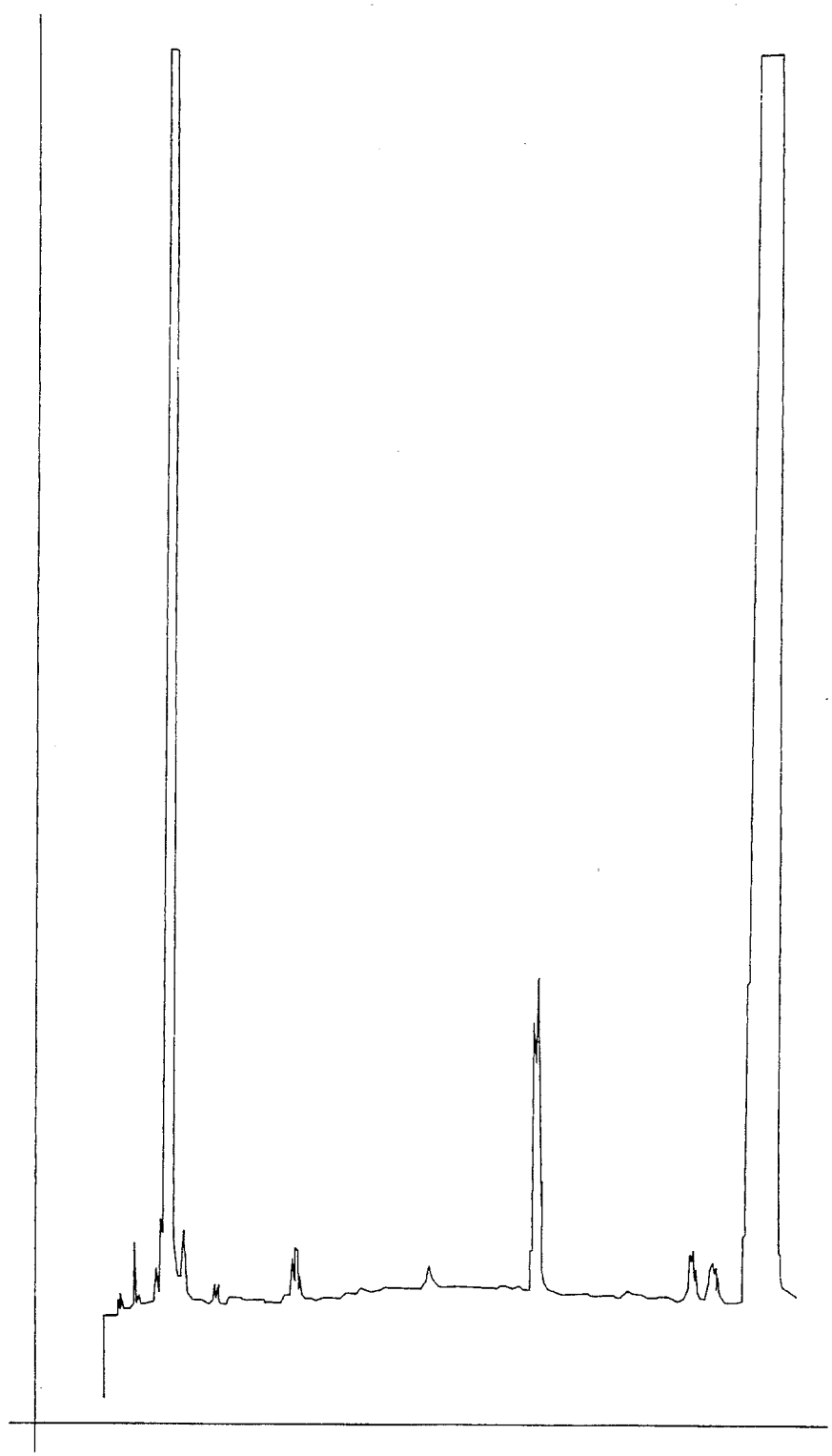
FIG. 1 is the capillary GC profile for the crude mixture produced according to the reaction of Example I(A) containing the compound having the structure.

Referring to FIG. 1, FIG. 1 is the capillary GC profile for the crude reaction product of Example I(A) (conditions: SE-30 column programmed from 100°–220° C. at 8° C. per minute). The peak indicated by reference numeral 10 is the peak for the compound having the structure:

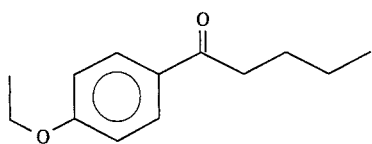

FIG. 3 is the capillary GC profile for the reaction product of Example I(B). The peak indicated by reference numeral 30 is the peak for the compound having the structure:

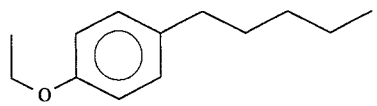

FIG. 5 is the capillary GC profile for the reaction product of Example I(C). The peak indicated by reference numeral 51 is the peak for the compound having the structure:

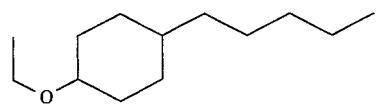

The peak indicated by reference numeral 52 is the peak for the compound having the structure:

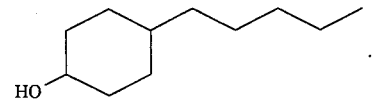

FIG. 7(A) is the capillary GC profile for the reaction product of Example II(A). The peak indicated by reference numeral 70 is the peak for the compound having the structure:

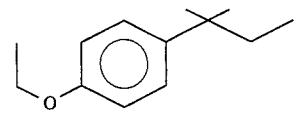

FIG. 8 is the capillary GC profile for the reaction product of Example II(B). The peak indicated by reference numeral 80 is the peak for the compound having the structure:

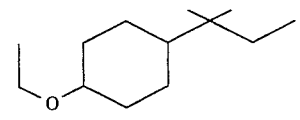

The peak indicated by reference numeral 81 is the peak for the compound having the structure:

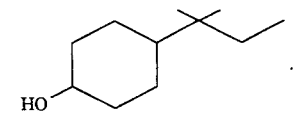

The peak indicated by reference numeral 82 is the peak for the compound having the structure:

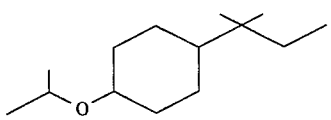

FIG. 10 is the capillary GC profile for the reaction product of Example III(A). The peak indicated by reference numeral 100 is the peak for the compound having the structure:

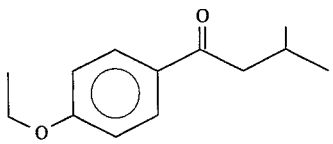

FIG. 12 is the capillary GC profile for the reaction product of Example III(B). The peak indicated by reference numeral 120 is the peak for the compound having the structure:

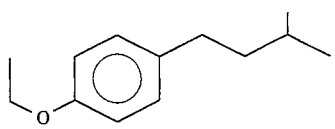

FIG. 14 is the capillary GC profile for the reaction product of Example III(C). The peak indicated by reference numeral 140 is the peak for the compound having the structure:

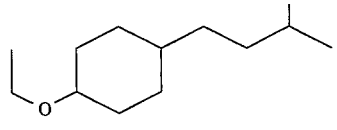

The peak indicated by reference numeral 141 is the peak for the compound having the structure:

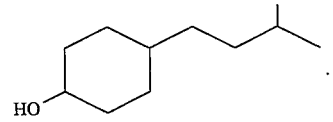

The peak indicated by reference numeral 142 is the peak for the compound having the structure:

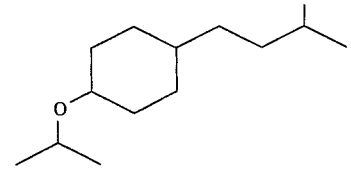

Referring to FIGS. 16 and 17, the apparatus used in producing polymeric fragrances containing the para-$C_5$ alkyl-substituted ethoxycyclohexanes of our invention comprises a device for forming scented polyolefin (for example) pellets, which comprises a vat or container 212 into which a mixture of polyolefin such as polyethylene and an aromatic substance or scented material is placed (in this case at least one of the para-$C_5$ alkyl-substituted ethoxycyclohexanes of our invention).

The container is closed by an air-tight lid 228 and the air-tight lid 228 is clamped to the container 212 by bolts 265.

A stirrer 273 traverses the lid or cover 228 in an air-tight manner and is rotated in a suitable manner.

Container 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with viscosity ranging between 180 and 220 Saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the para-$C_5$ alkyl-substituted ethoxycyclohexanes of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the para-$C_5$ alkyl-substituted ethoxycyclohexanes of our invention) are added to the polyolefin.

After the scent imparting material (e.g., a composition containing at least one of the para-$C_5$ alkyl-substituted ethoxycyclohexanes of our invention) is added to the container 212, the mixture is stirred for a few minutes, for example, 5–15 minutes, and maintained within the temperature range as indicated, supra, by means of heating coils 212A.

The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter, the valve "V" is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e.g., at least one of the para-$C_5$ alkyl-substituted ethoxycyclohexanes of our invention) will continuously drop through orifices 234 downwardly from conduit 232. During this time, the temperature of the polymer (e.g., polyolefin) and scent imparting material (e.g., a mixture containing at least one of the para-$C_5$ alkyl-substituted ethoxycyclohexanes of Our invention) is accurately controlled so that a temperature in the range of from about 210°–275° F. will exist in the conduit 218/232. The regulation of the temperature through controls 216 and 220 is essential in order to insure temperature balance to provide for the continuous dropping or dripping of molten polymer (e.g., polyethylene) and scenting material (e.g., one or more of the para-$C_5$ alkyl-substituted ethoxycyclohexanes of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor belt 238, they form pellets 244 which harden almost instantaneously and fall off the end of the conveyor belt 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The conveyor belt 238 is advantageously fabricated of a material which will not normally stick to a melted plastic but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the conveyor belt 238.

THE INVENTION

The present invention provides para-$C_5$ alkyl-substituted ethoxycyclohexanes defined according to the structure:

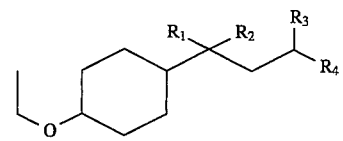

wherein $R_1$, $R_2$ and $R_3$ are the same or different methyl or hydrogen; and wherein $R_4$ represents hydrogen, methyl or ethyl with the proviso that the sum of the number of carbon atoms in $R_1$, $R_2$, $R_3$ and $R_4$ is 2.

The compositions of matter of our invention produced according to the processes of our invention are capable of augmenting, enhancing or providing green, fresh cut grass-like, citrus, privet hedge (*Ligustrum vulgare*)-like, woody, floral, muguet, rose petal, balsamic and tomato leaf aromas with green, ozoney, woody, floral, muguet, rose, powdery, robusta coffee, dark cocoa, fruity, fatty-oily and tomato leaf topnotes and linden blossom, cucumber and melon-like undertones to perfume compositions, colognes and perfumed articles (e.g., solid or liquid anionic, cationic, nonionic or zwitterionic detergents, fabric softener articles, dryer-added fabric softener articles, fabric softener compositions, cosmetic powders, hair preparations, perfumed polymers and the like).

The substances of our invention are prepared in the alternative by (i) reacting phenetole (ethoxybenzene) having the structure:

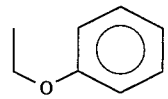

with an acyl derivative defined according to the structure:

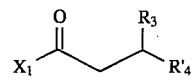

according to the reaction:

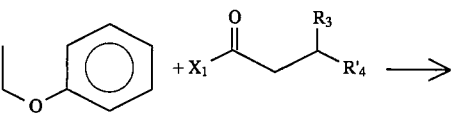

-continued

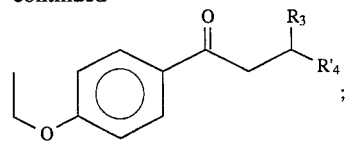

then reducing the resulting ketone according to the reaction:

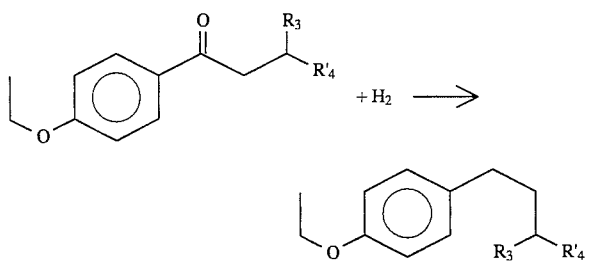

in the presence of an appropriate catalyst; and finally, reducing the resulting para ethoxyalkylbenzene derivative according to the reaction:

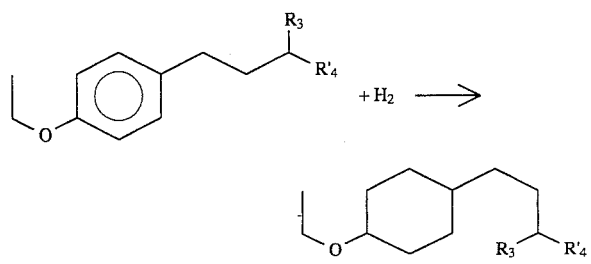

also in the presence of an appropriate catalyst under appropriate reaction conditions; or (ii) reacting an alkyl phenol having the structure:

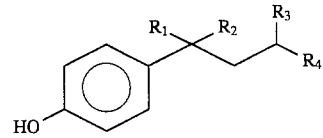

with base having the structure:

$M_{C_P}^{\oplus}$ (OH⁻)

(or having the structure:

$M_C (OH)_P$ in order to form a salt having the structure:

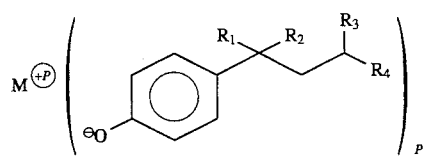

according to the reaction:

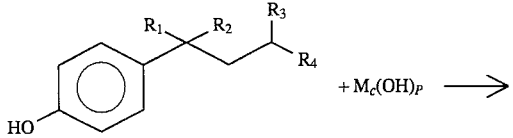

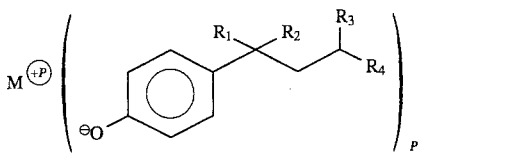

and then reacting the resulting salt having the structure:

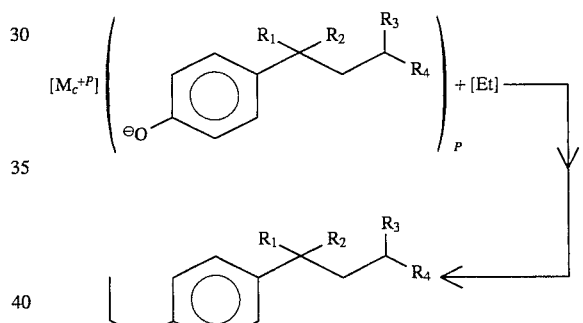

with an ethoxylating reagent indicated by the symbol:

[et]

according to the reaction:

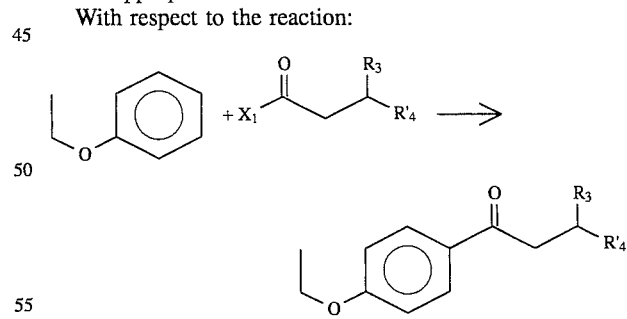

under appropriate reaction conditions.
With respect to the reaction:

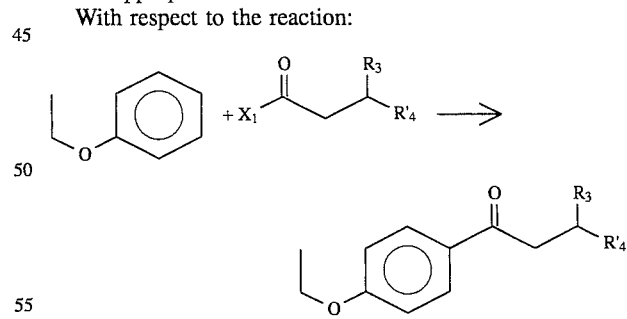

in the compound having the structure:

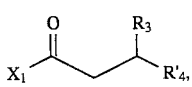

$X_1$ is chloro, bromo or hydroxy; $R_3$ is hydrogen or methyl and $R_4'$ is ethyl or methyl with the proviso that the sum of the carbon atoms in $R_3$ and $R_4'$ is 2. Furthermore, with respect to the reaction:

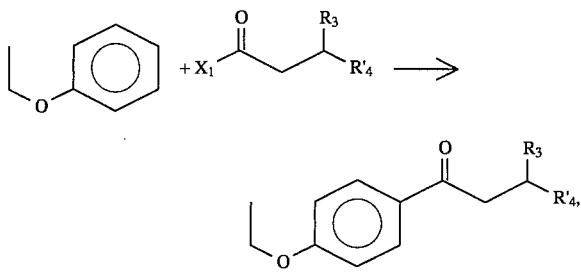

this reaction takes place in the presence of a Lewis acid catalyst having the structure:

or having the structure:

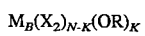

in the presence of a solvent or in the absence of a solvent. The compound having the structure:

is a metal halide wherein $M_A$ is a metal such as boron, aluminum, iron, tin or zinc. The halide $X_2$ is chloro, bromo, iodo or fluoro. N is is the valence of the metal $M_A$. Examples of the compound or Lewis acid catalyst having the structure:

are boron trifluoride, aluminum trichloride, ferric chloride, stannic chloride or zinc chloride. On the other hand, the catalyst useful in the practice of our invention may be a complex such as boron trifluoride etherate, to wit:

$BF_3\,(C_2H_5OC_2H_5)$.

Furthermore, the Lewis acid catalyst useful in the practice of our invention may have the structure:

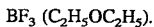

wherein $M_B$ is a metal such as aluminum; wherein $X_2$ is a halide such as chloro; and R represents lower alkyl such as methyl, ethyl or isopropyl. N is the valence of the metal $M_B$ and K represents the number of alkoxy moieties wherein:

$0<K<N$ and wherein:

$N\leq 4$.

As stated, supra, the reaction may take place in the presence of or absence of a solvent. Examples of solvents are 2-nitropropane having the structure:

(the most preferred solvent); nitromethane, hydrocarbons or chlorinated hydrocarbons.

The temperature of reaction may be between about 0° C. up to about 40° C. with a preferred temperature range of from about 0° C. up to about 5° C.

The preferred reactants of the genus:

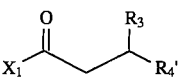

are those where $X_1$ is chloro due to economic reasons.

At the end of the reaction, the reaction mass is distilled in order to yield substantially pure materials defined according to the structure:

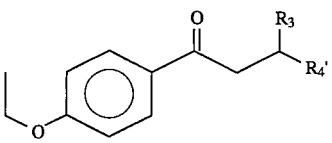

wherein $R_3$ represents hydrogen or methyl and $R_4'$ represents ethyl or methyl with the proviso that the sum of the carbon atoms in $R_3$ and $R_4'$ is 2.

The compounds having the structure:

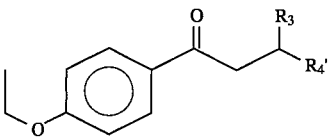

are then further reacted by means of reduction using hydrogen and an appropriate hydrogenation catalyst according to the reaction:

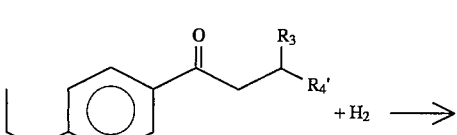

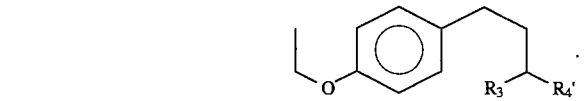

The hydrogenation catalyst may be palladium on carbon, platinum, palladium, Raney nickel or rhodium. A preferred catalyst is 1% palladium on carbon. Copper chromite catalysts are also useful. This reaction takes place at a temperature of between 105° up to about 120° C. in a solvent, preferably isopropyl alcohol and at a pressure in the range of from about 200 psig (pounds per square inch gauge) up to about 450 psig with a preferred reaction pressure of 400 psig. Thus, examples of the preferred reaction of this aspect of the process of our invention are as follows:

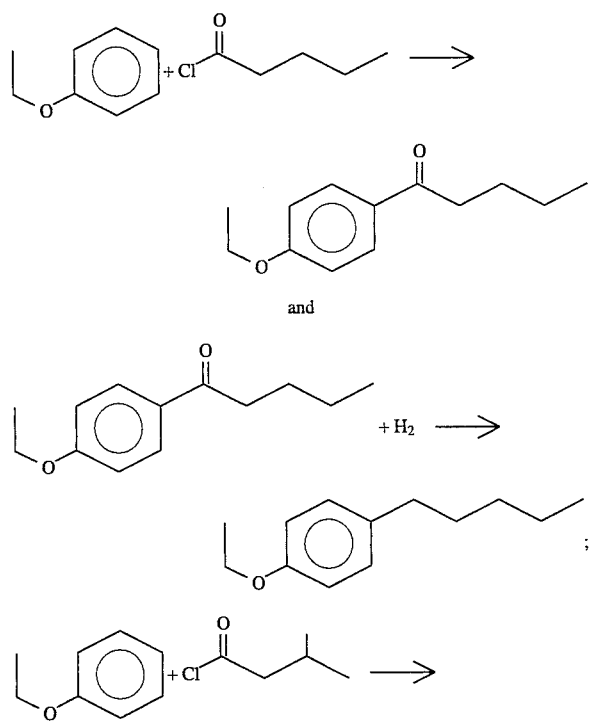

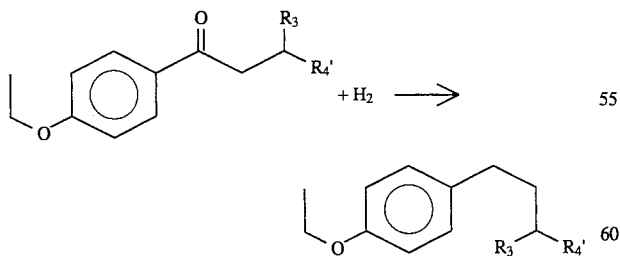

The time of reaction of this first hydrogenation step is between 110 and 140 minutes. Furthermore, the reaction, to wit:

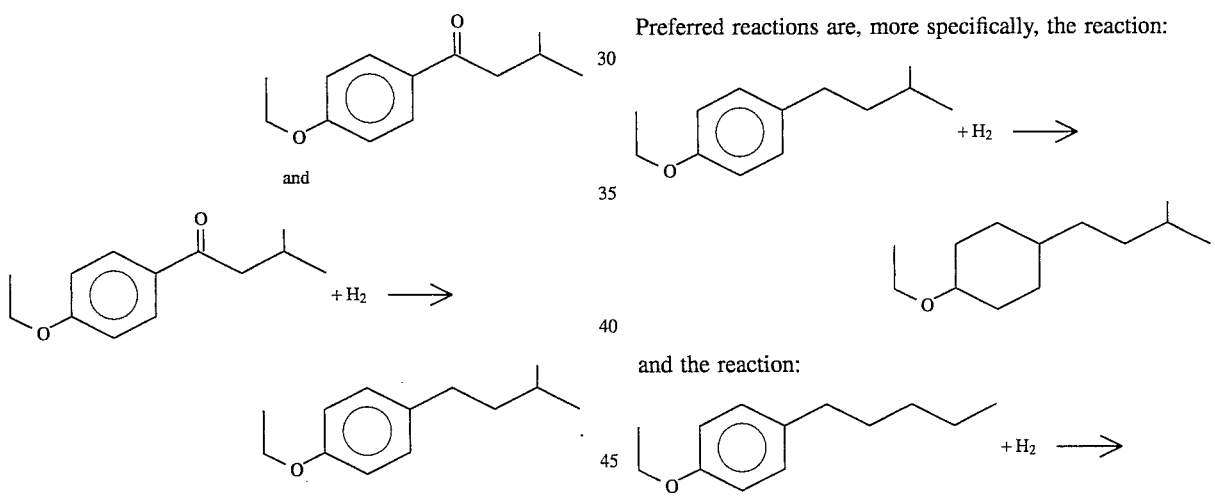

must take place in the presence of a proton source. Examples of a proton source are FILTROL®, an acid ion exchange composition; or phosphoric acid or citric acid.

The compounds having the structure:

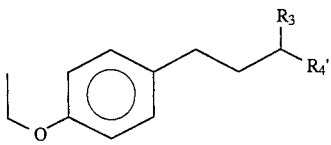

thus produced are recovered from the reaction mass and further hydrogenated using 3% ruthenium on carbon catalysts at a temperature in the range of from 110° up to 145° C. and at a pressure in the range of from 400 up to 700 psig for a period of time of from 0.25 up to 10 hours according to the reaction:

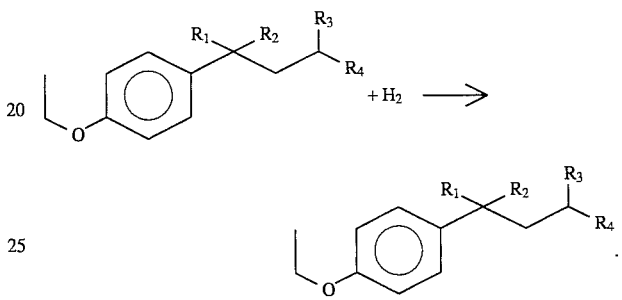

Preferred reactions are, more specifically, the reaction:

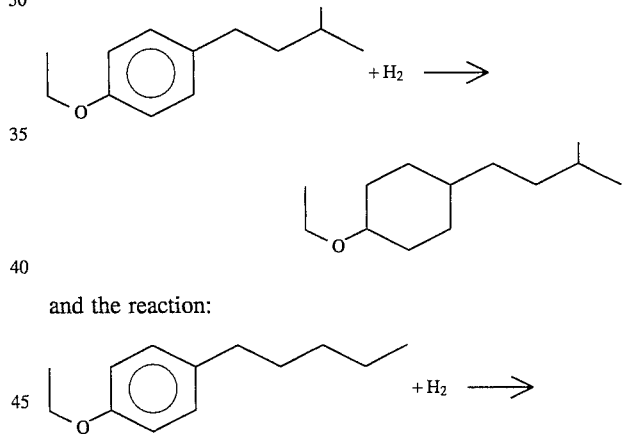

and the reaction:

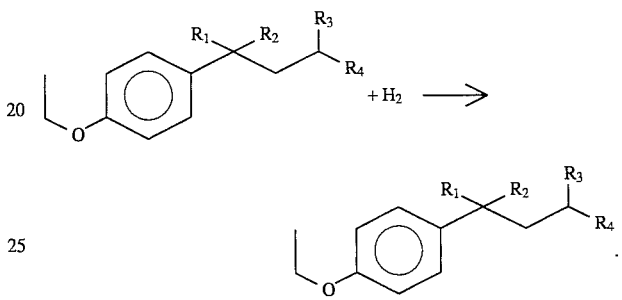

With reference to the reaction sequence:

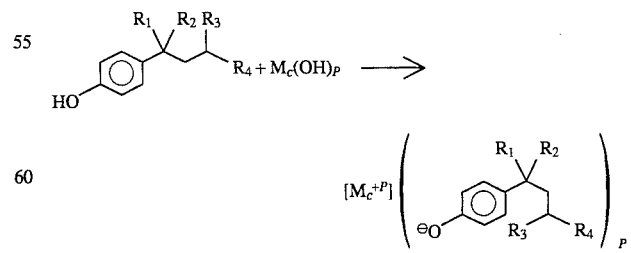

and

-continued

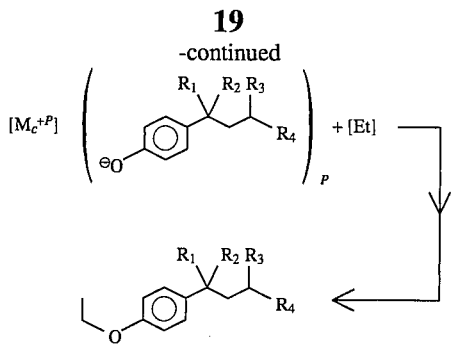

in the compound having the structure:

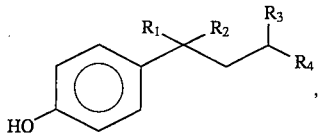

$R_1$, $R_2$ and $R_3$ are the same or different and each represents methyl or hydrogen; and $R_4$ represents hydrogen, methyl or ethyl with the proviso that the sum of the number of carbon atoms in $R_1$, $R_2$, $R_3$ and $R_4$ is 2. In the compound:

also shown as:

$M_c$ represents an alkali metal such as sodium, potassium or lithium or an alkaline earth metal such as calcium or magnesium. When $M_c$ represents an alkali metal, P is 1 and when $M_c$ is an alkaline earth metal, P is 2. Preferably, $M_c$ is sodium. Preferably, the ethoxylation reagent is diethyl sulfate, although ethoxylation reagents such as ethyl chloride, ethyl bromide and ethyl iodide are also useful ethoxylation reagents.

Preferred reaction sequences concerning the foregoing reaction sequence are:

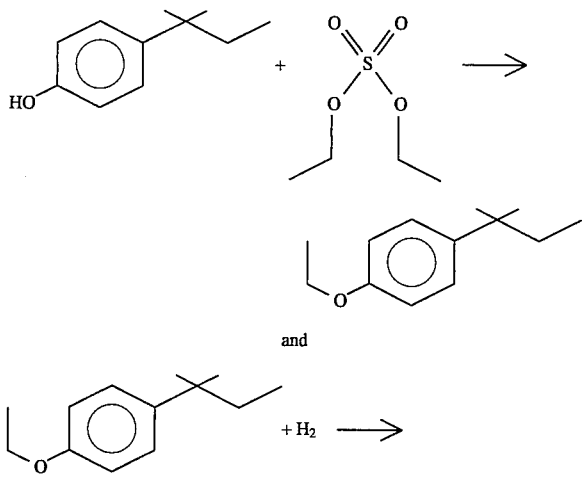

-continued

An additional ethoxylation reagent is a mixture of ethyl alcohol and 93% concentrated sulfuric acid with the ratio of the ethyl alcohol:concentrated sulfuric acid being 50:50 (weight:weight).

With respect to the reaction:

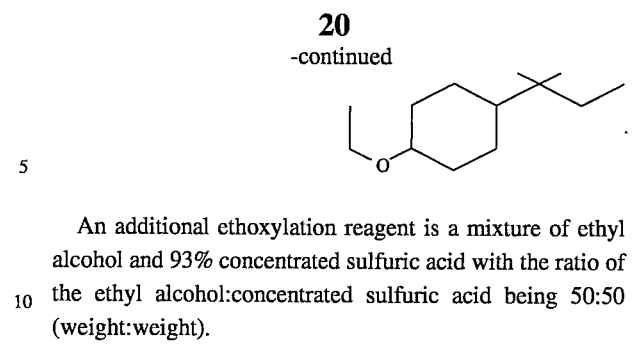

or for that matter, the generic reaction:

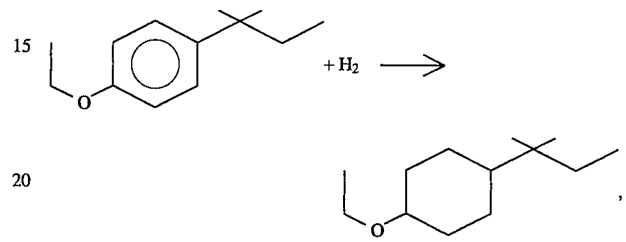

this reaction takes place in the presence of a 3% ruthenium/carbon catalyst at 110°–145° C.; a pressure of 400–700 psig and a time of reaction of from 0.25 up to 10 hours.

Alternatively, other ruthenium-based hydrogenation catalysts may be used and these ruthenium-based hydrogenation catalysts are disclosed and claimed in U.S. Pat. No. 5,403,805 issued on Apr. 4, 1995, the specification for which is incorporated herein by reference. Furthermore, other ruthenium-based catalysts can be used, for example, those set forth in U.S. Pat. No. 5,426,216 issued on Jun. 20, 1995, the specification for which is incorporated by reference herein.

Palladium on carbon catalysts for the reaction:

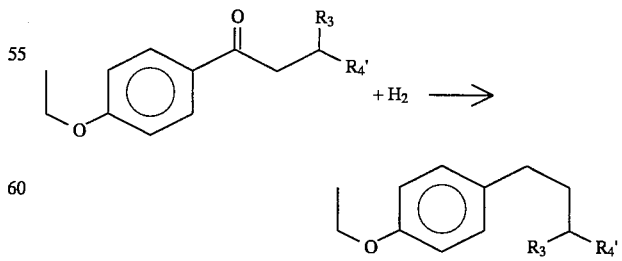

useful in carrying out our invention are set forth in published European Patent Application No. 616,994, published on Sep. 28, 1994.

With respect to the reaction:

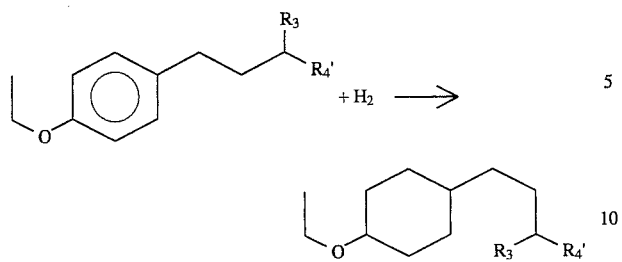

as well as the reaction:

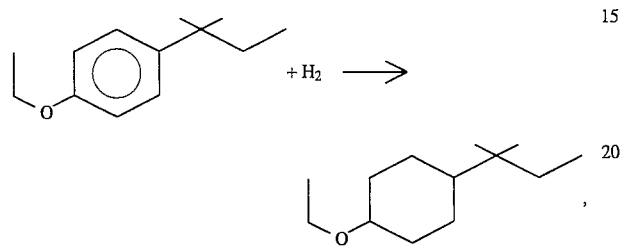

the conditions of the reaction dictate the nature of the resultant product insofar as the isomers of the resulting product are concerned. Thus, the ratio of "cis:trans" and the ratio of optical isomers obtained is a function of the conditions of reaction. For example, the isomers of the compound having the structure:

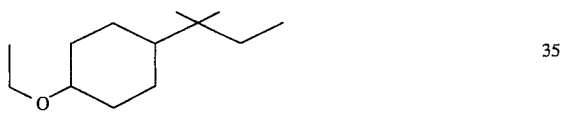

are as follows:

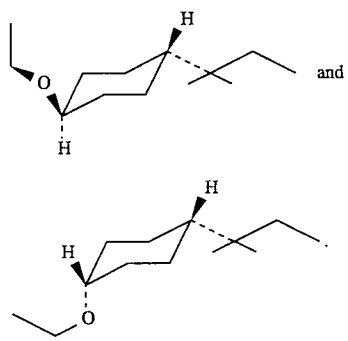

Isomers of the compound having the structure:

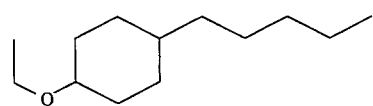

are as follows:

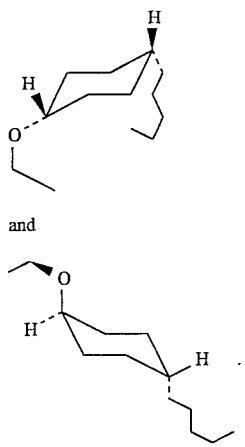

and

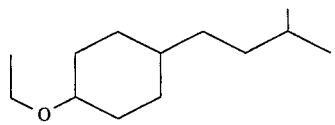

Isomers of the compound having the structure:

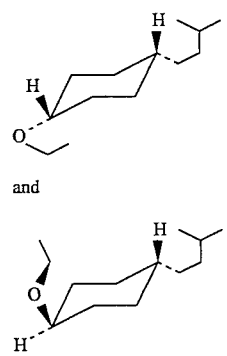

are as follows:

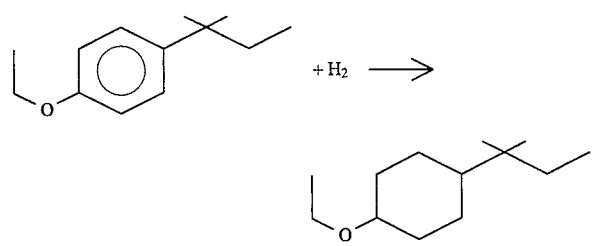

Each of the foregoing isomers has optical isomers thereof. Thus, for example, in carrying out the reaction:

according to Example II(B) in the presence of a 3% ruthenium on carbon catalyst when the reaction takes place at a temperature in the range of 110°–120° C. at a pressure of 600 psig for a period of time of 6.5 hours in the presence of an isopropanol solvent, where the 3% ruthenium on carbon catalyst:reactant having the structure:

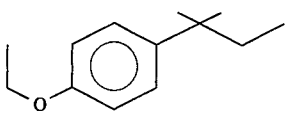

is 0.03:1 and the ratio of solvent:reactant having the structure:

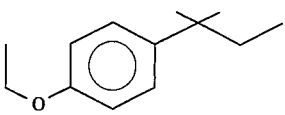

is 0.088, the weight ratio of reaction products having the structures:

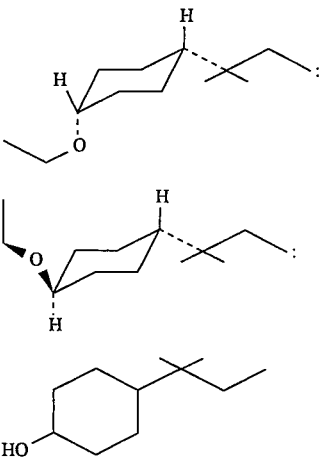

is 85:10:5, respectively.

With respect to the etherification reaction:

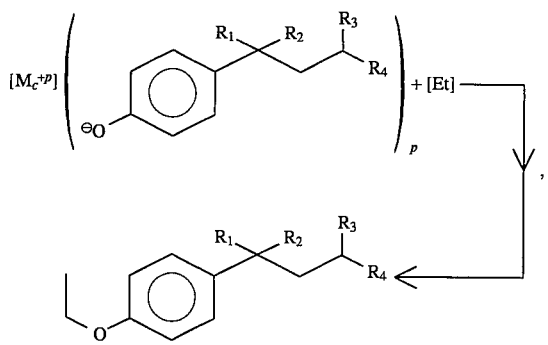

this etherification reaction preferably takes place in the presence of a "phase transfer reagent" such as ALIQUAT® 336 (trademark of the Henkel Corporation of Minneapolis, Minn.), tricapryl methyl ammonium chloride having the structure:

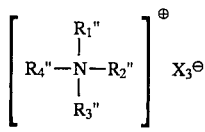

wherein $R_1''$, $R_2''$ and $R_3''$ represent capryl; $X_3$ represents chloro; and $R_4''$ is methyl. Other phase transfer reagents may also be used wherein X represents chloro or bromo; $R_1'$, $R_2''$ and $R_3''$ are the same or different $C_6$–$C_{10}$ alkyl and $R_4''$ represents $C_1$–$C_3$ alkyl.

The etherification reaction may take place in the presence of a calcium phenate catalyst having the structure:

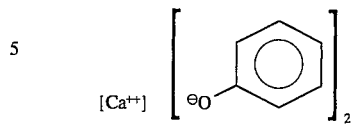

in accordance with the procedure of the People's Republic of China Patent No. 1,023,643 (PCT Patent Application No. 91 CN 108 407 assigned to the China Petrochemical General Corporation having DERWENT Excession No. 93-101478/13.

The following Table I sets forth the perfumery properties of various compositions of matter so useful in the perfumery of our invention.

TABLE I

| Description of Composition | Perfumery Properties |
|---|---|
| The compound having the structure:<br><br>prepared according to Example I(C) distillation fraction No. 8. | A green, citrus, ozoney, privet hedge (*Ligustrum vulgare*)-like aroma. |
| The compound having the structure:<br><br>prepared according to Example II(B) bulked distillation fraction Nos. 6–14. | A green (fresh cut grass-like), woody, floral (muguet), balsamic aroma with green, ozoney, woody, floral (muguet) topnotes and linden blossom, cucumber, melon-like undertones. |
| The compound having the structure:<br><br>prepared according to Example III(C) bulked distillation fractions Nos. 5–8 | A floral (rose petal), tomato leaf, green, muguet aroma with powdery, floral (rose), green, muguet, robusta coffee, dark cocoa, fruity, tomato leaf and fatty-oily topnotes. |

One or more of the para-$C_5$ alkyl-substituted ethoxycyclohexanes prepared in accordance with the process of our invention and one or more auxiliary perfume ingredients including, for example, alcohols, aldehydes, ketones, terpenic hydrocarbons, nitriles, esters, lactones, ethers other than the ethers of our invention, natural essential oils and synthetic essential oils may be admixed so that the combined odors of the individual components produce a pleasant and desired fragrance, particularly and preferably in the citrus, fruity and woody types of fragrances. Such compositions usually contain:

(a) the main note or the "bouquet" or foundation stone of the composition;

(b) modifiers which round off and accompany the main note;

(c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute their particular olfactory characteristics, however, the overall sensory effect of the perfume compositions will be at least the sum total of the effects of each of the ingredients. Thus, the para-$C_5$ alkyl-substituted ethoxycyclohexanes of our invention produced in accordance with the processes of our invention can be used to alter, modify or enhance the aroma characteristics of a perfume composition, for example, by utilizing or moderating the olfactory reaction contributed by another ingredient in the composition. In the alternative, the para-$C_5$ alkyl-substituted ethoxycyclohexanes of our invention can be used to formulate a perfume composition by themselves.

The amount of the para-$C_5$ alkyl-substituted ethoxycyclohexanes prepared in accordance with the processes of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of the para-$C_5$ alkyl-substituted ethoxycyclohexanes prepared in accordance with the processes of our invention or even less (e.g., 0.005%) can be used to impart, augment or enhance green, fresh cut grass-like, citrus, ozoney, privet hedge (*Ligustrum vulgare*)-like, woody, floral, muguet, rose petal, balsamic and tomato leaf aromas with green, ozoney, woody, floral, muguet, rose, powdery, robusta coffee, dark cocoa, fruity, fatty-oily and tomato leaf topnotes and linden blossom, cucumber and melon-like undertones to soaps, cosmetics, anionic, cationic, nonionic or zwitterionic detergents, fabric softener articles, micorporous polymers, particularly acrylic resins, polyethylenes and other products. The amount employed can range up to 100% of the fragrance components and will depend on considerations of cost, nature of the end product, the effect desired on the finished product and the particular fragrance sought.

The para-$C_5$ alkyl-substituted ethoxycyclohexanes of our invention prepared in accordance with the processes of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens; powders such as talcs, dusting powders, face powders, microporous "perfumed" slow release polymers and the like.

When used as (an) olfactory component(s) in perfumed articles, as little as 0.005% of the para-$C_5$ alkyl-substituted ethoxycyclohexanes prepared in accordance with the processes of our invention, will suffice to impart, augment or enhance green, fresh cut grass-like, citrus, ozoney, privet hedge (*Ligustrum vulgare*)-like, woody, floral, muguet, rose petal, balsamic and tomato leaf aromas with green, ozoney, woody, floral, muguet, rose, powdery, robusta coffee, dark cocoa, fruity, fatty-oily and tomato leaf topnotes and linden blossom, cucumber and melon-like undertones. Generally no more than 6% of the para-$C_5$ alkyl-substituted ethoxycyclohexanes of our invention based on the ultimate end product is required in the perfumed article. Accordingly, the range of use of the para-$C_5$ alkyl-substituted ethoxycyclohexanes of our invention in perfumed articles, per se, is from about 0.005% up to about 6% by weight based on the perfumed article.

In addition, the perfume composition or fragrance composition of our invention can contain a vehicle or carrier for the para-$C_5$ alkyl-substituted ethoxycyclohexanes prepared in accordance with the processes of our invention. The vehicle can be a liquid such as a non-toxic alcohol, e.g., ethyl alcohol; a non-toxic glycol, e.g., propylene glycol or dipropylene glycol or the like. The carrier can be an absorbent solid such as a gum (e.g., gum arabic, guar gum or xanthan gum or combinations thereof) or components for encapsulating the composition (such as by coacervation) or using prepolymers such as urea-formaldehyde prepolymers which are able to form a urea-formaldehyde polymer capsule around a liquid perfume center.

It will thus be apparent that the para-$C_5$ alkyl-substituted ethoxycyclohexanes prepared in accordance with the processes of our invention can be utilized to alter, modify or enhance sensory properties particularly organoleptic properties such as fragrances of a wide variety of consumable materials.

The following Examples I, II and III set forth means for preparing the para-$C_5$ alkyl-substituted ethoxycyclohexanes of our invention. The examples including and following Example IV, infra, set forth illustrations of organoleptic utilities of the para-$C_5$ alkyl-substituted ethoxycyclohexanes of our invention.

All parts and percentages given herein are by weight unless otherwise specified.

EXAMPLE I

PREPARATION OF ETHYL 4-PENTYLCYCLOHEXYL ETHER

EXAMPLE I (A)

Reaction:

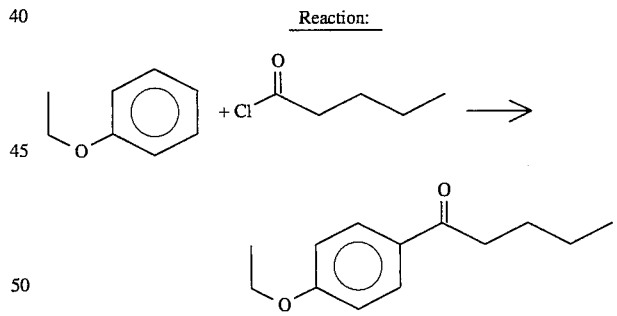

Into a 2 liter reaction vessel equipped with stirrer, thermometer and cooling coils are placed 450 ml of 1-nitropropane (NIPAR®). The nitropropane is cooled to a temperature of 0°–8° C.

350 Grams of anhydrous aluminum chloride is slowly added to the nitropropane.

Over a period of 0.25 hours, 290 grams of ethoxybenzene having the structure:

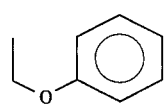

is added to the reaction mass.

Over a 2 hour period, 300 grams of the compound having the structure:

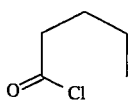

is added to the reaction mass with stirring.

The reaction mass is then stirred for a period of 30 minutes at 0°–8° C. The resulting reaction mass is then quenched onto 1 liter of a mixture of ice and water.

The resulting product exists now in two phases: an organic phase and an aqueous phase. The organic phase is separated from the aqueous phase and the organic phase is washed with equal volumes, consecutively, of sodium bicarbonate (saturated aqueous solution), water and saturated aqueous sodium chloride. The organic phase is then dried over anhydrous magnesium sulfate and filtered. The filtrate is then "rushed over" yielding 307 grams of product, distilled as follows:

| Fraction Number | Vapor Temperature (°C.) | Liquid Temperature (°C.) | Vacuum mm/Hg Pressure |
|---|---|---|---|
| 1 | 21/76 | 21/76 | 100/3 |
| 2 | 131 | 133 | 1.6 |
| 3 | 156 | 200 | 2.4 |

EXAMPLE I(B)

Reaction:

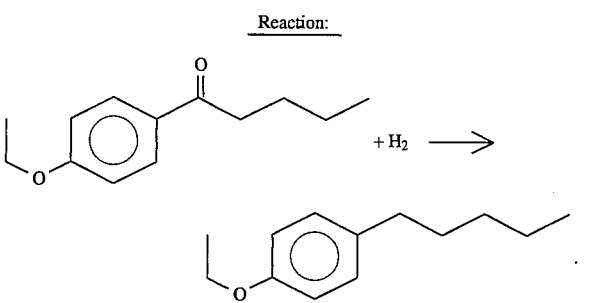

Into a 1 liter autoclave equipped for high pressure are charged the following materials:

255 grams of the compound having the structure:

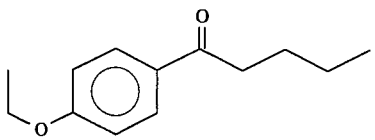

prepared according to Example I(A), supra;
230 grams of isopropyl alcohol; and
3 grams of 1% palladium on carbon.

The autoclave is sealed and heated to a temperature of 115°–120° C. Hydrogen feed is commenced and the autoclave is pressurized at 400 psig using hydrogen. The autoclave, with shaking, is pressurized at 400 psig hydrogen for a period of 2 hours. At the end of the 2 hour period, the autoclave temperature is raised to 120°–125° C. while maintaining the 400 psig pressure. The temperature is maintained at 120°–125° C. for a period of 1 hour.

At the end of the 1 hour period, the hydrogen feed is ceased; the autoclave is cooled, depressurized and opened. The resulting product is filtered and the resulting filtrate is fractionally distilled yielding the following fractions:

| Fraction Number | Vapor Temperature (°C.) | Liquid Temperature (°C.) | Vacuum mm/Hg Pressure |
|---|---|---|---|
| 1 | 25/28 | 23/110 | 150/30 |
| 2 | 94 | 120 | 1 |
| 3 | 91 | 118 | 0.8 |
| 4 | 91 | 118 | 0.8 |
| 5 | 91 | 118 | 0.8 |
| 6 | 92 | 118 | 0.8 |
| 7 | 92 | 118 | 0.8 |
| 8 | 92 | 118 | 0.8 |
| 9 | 92 | 126 | 0.8 |
| 10 | 44 | 175 | 0.6 |

Fractions 5–9 were bulked. Fractions 5–9 are the compound having the structure:

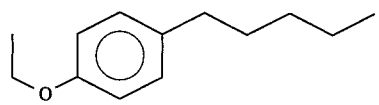

as confirmed by NMR, IR and mass spectral analyses.

EXAMPLE I(C)

Reaction:

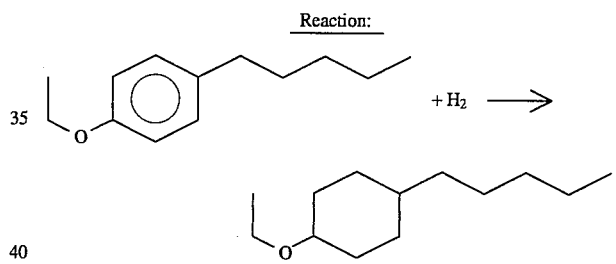

Into a 500 cc autoclave is placed 125 grams of the compound having the structure:

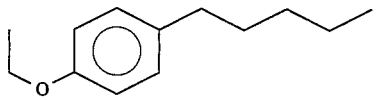

prepared according to Example I(B);
15 grams anhydrous isopropyl alcohol; and
4 grams of 3% ruthenium on carbon.

The autoclave is sealed and heated to 110°–115° C. and pressurized with hydrogen to 400 psig hydrogen.

The autoclave with hydrogen feed is run for a period of 11 hours at 110°–115° C. at 400 psig.

At the end of the reaction, the autoclave is cooled and opened and the contents are filtered. The isopropyl alcohol is stripped and the resulting product is mixed with propionic anhydride (50 grams) and refluxed for a period of 1.5 hours.

The resulting product is quenched with an equal volume of water and washed with an equal volume of saturated sodium carbonate.

The resulting product is then fractionally distilled yielding the following fractions:

| Fraction Number | Vapor Temperature (°C.) | Liquid Temperature (°C.) | Vacuum mm/Hg Pressure |
|---|---|---|---|
| 1 | 21/33 | 23/100 | 120/4 |
| 2 | 88 | 118 | 4 |
| 3 | 106 | 118 | 4 |
| 4 | 107 | 118 | 4 |
| 5 | 107 | 118 | 4 |
| 6 | 105 | 118 | 4 |
| 7 | 104 | 120 | 4 |
| 8 | 104 | 120 | 4 |
| 9 | 106 | 124 | 4 |
| 10 | 105 | 126 | 4 |
| 11 | 105 | 128 | 4 |
| 12 | 107 | 132 | 4 |
| 13 | 106 | 140 | 4 |
| 14 | 95 | 140 | 0.8 |

Fraction 8 is the compound having the structure:

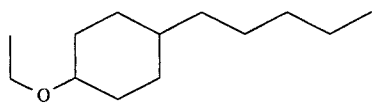

as confirmed by NMR, IR and mass spectral analyses.

EXAMPLE II

PREPARATION OF ETHYL 4-(1',1'-DIMETHYLPROPYL)CYCLOHEXYL ETHER EXAMPLE II(A)

Reactions:

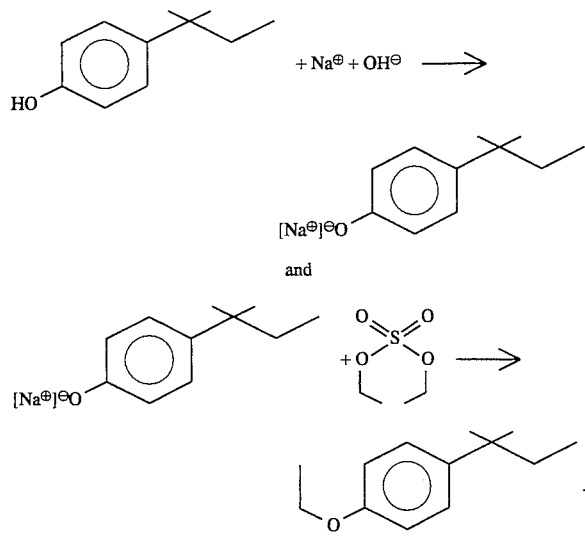

Summary Reaction:

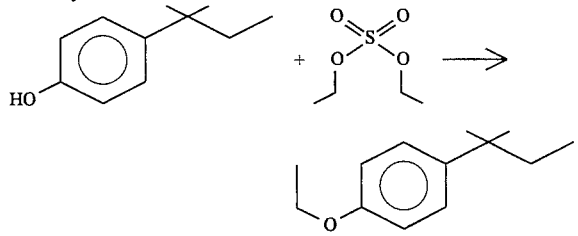

Into a 2 liter reaction vessel equipped with stirrer, thermometer, reflux condenser and heating mantle are placed the following ingredients:

sodium hydroxide—156 grams;

water—468 grams; and

ALIQUAT® 336—25 grams.

The resulting mixture is heated to 45° C.

Over a period of 1 hour, 500 grams of t-amylphenol having the structure:

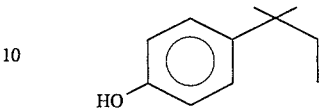

is added to the reaction mass with stirring while maintaining the temperature at 45° C.

Over a period of 2 hours while maintaining the reaction mass at 45° C., diethyl sulfate having the structure:

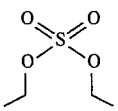

is added to the reaction mass. The reaction mass is maintained at 45° C. with stirring for an additional 3 hour period.

At the end of the 3 hour period, 500 grams of 25% aqueous sodium hydroxide is added to the reaction mass and heated at 45° C. for a period of 1 hour.

At the end of the 1 hour period, the reaction mass is cooled to room temperature and the reaction mass now exists in two phases: an organic phase and an aqueous phase. The organic phase is admixed with 50 ml of toluene. The organic phase is then dried over anhydrous magnesium sulfate. The resulting product is then admixed with 40 grams of propionic anhydride and the resulting mixture is heated to 100° C. and maintained at 100° C. with stirring for a period of 0.5 hours. The resulting product is then cooled to 60° C. and admixed with 100 ml water. The resulting product now exists in two phases: an organic phase and an aqueous phase. The organic phase is separated from the aqueous phase and the organic phase is washed, consecutively, with an equal volume of saturated aqueous sodium chloride followed by saturated aqueous sodium bicarbonate. The resulting product is dried over anhydrous magnesium sulfate and fractionally distilled yielding the following fractions:

| Fraction Number | Vapor Temperature (°C.) | Liquid Temperature (°C.) | Vacuum mm/Hg Pressure | Reflux Ratio |
|---|---|---|---|---|
| 1 | 20/85 | 20/105 | 0.8/0.8 | 4:1 |
| 2 | 84 | 103 | 0.67 | 9:1 |
| 3 | 84 | 104 | 0.59 | 9:1 |
| 4 | 84 | 103 | 0.56 | 9:1 |
| 5 | 84 | 103 | 0.55 | 9:1 |
| 6 | 83 | 104 | 0.55 | 9:1 |
| 7 | 83 | 104 | 0.53 | 9:1 |
| 8 | 83 | 104 | 0.53 | 9:1 |
| 9 | 86 | 104 | 1.1 | 9:1 |
| 10 | 83 | 101 | 0.7 | 9:1 |
| 11 | 88 | 104 | 1.03 | 9:1 |
| 12 | 88 | 104 | 1.06 | 9:1 |
| 13 | 89 | 105 | 1.07 | 9:1 |
| 14 | 88 | 107 | 1.06 | 4:1 |
| 15 | 89 | 116 | 1.07 | 4:1 |

The resulting product has the structure:

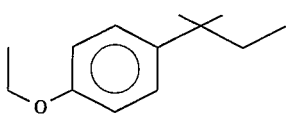

as confirmed NMR, IR and mass spectral analyses.

EXAMPLE II(B)

Reaction:

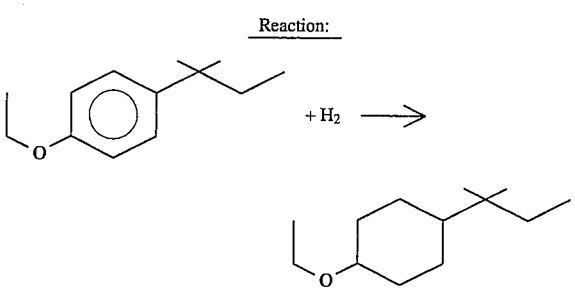

Into a 1 liter autoclave equipped with a hydrogen pressurization tube are place the following materials:

295 grams of the compound having the structure:

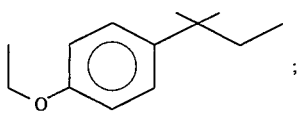

8.8 grams 3% ruthenium on carbon; and 100 grams anhydrous isopropyl alcohol.

The autoclave is sealed and pressurized with hydrogen. The temperature of the autoclave is raised to 110°–120° C. and pressurized at 600 psig with hydrogen. The hydrogen pressurization continues for a period of 6.5 hours at a temperature of 110°–120° C.

At the end of the 6.5 hour period, the autoclave is cooled and opened and the contents are filtered.

The resulting filtrate is distilled using a fractional distillation column yielding the following fractions:

| Fraction Number | Vapor Temperature (°C.) | Liquid Temperature (°C.) | Vacuum mm/Hg Pressure |
|---|---|---|---|
| 1 | 23/30 | 23/105 | 100/30 |
| 2 | 91 | 106 | 3 |
| 3 | 97 | 112 | 3 |
| 4 | 96 | 112 | 4 |
| 5 | 97 | 115 | 4 |
| 6 | 95 | 115 | 4 |
| 7 | 95 | 118 | 3.5 |
| 8 | 99 | 118 | 4.0 |
| 9 | 100 | 122 | 4.0 |
| 10 | 99 | 126 | 3.0 |
| 11 | 100 | 133 | 3.0 |
| 12 | 94 | 190 | 1.1 |
| 13 | 94 | 192 | 1.0 |
| 14 | 94 | 193 | 1.0 |
| 15 | 82 | 212 | 0.8 |

Fractions 6–14 are bulked. Fractions 6–14 consist of the compound having the structure:

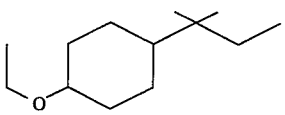

and a small quantity of the compound having the structure:

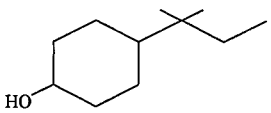

with the ratio of isomers being 85 parts by weight of the compound having the structure:

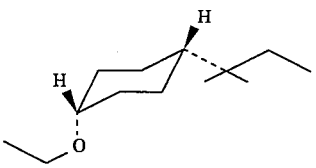

10 parts by weight of the compound having the structure:

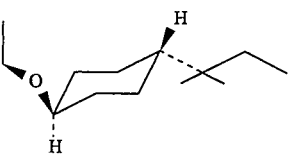

5 parts by weight of the compound having the structure:

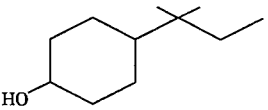

EXAMPLE III

PREPARATION OF ETHYL 4-(3'-METHYLBUTYL)CYCLOHEXYL ETHER

EXAMPLE III(A)

Reaction:

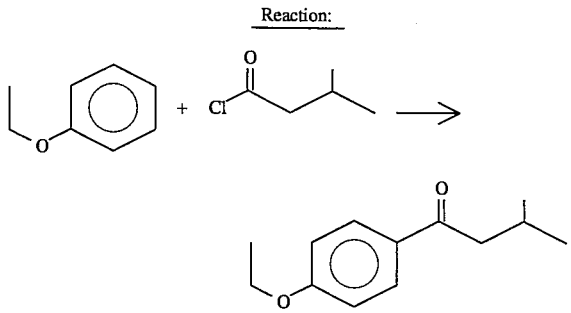

Into a 2 liter reaction vessel equipped with stirrer, thermometer, reflux condenser and cooling coils are placed 500 grams of 1-nitropropane (NIPAR®). The 1-nitropropane is cooled to 0° C.

Over a period of 1 hour while maintaining the temperature of the reaction mixture at 0°–10° C., 496 grams of anhydrous aluminum chloride is added to the reaction mass.

The reaction mass is cooled to 0° C. and while maintaining the reaction mass at 0° C., over a period of 0.33 hours, 393 grams of ethoxybenzene having the structure:

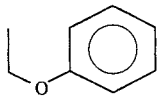

is added to the reaction mass.

While maintaining the reaction mass at 0°–10° C. over a period of 1 hour, 425 grams of the compound having the structure:

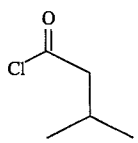

is added to the reaction mass. The reaction mass is then stirred at 0°–10° C. for a period of 0.5 hours.

The reaction mass is then added to 1 liter of a mixture of ice and water. The resulting mixture now exists in two phases: an organic phase and an aqueous phase. The organic phase is separated from the aqueous phase and dried over anhydrous magnesium sulfate. The resulting mixture is filtered and the resulting product is distilled in a fractional distillation column yielding the following fractions:

| Fraction Number | Vapor Temperature (°C.) | Liquid Temperature (°C.) | Vacuum mm/Hg Pressure |
|---|---|---|---|
| 1 | 80/69 | 21/109 | 110/1 |
| 2 | 60 | 129 | 0.8 |
| 3 | 112 | 145 | 0.8 |
| 4 | 122 | 147 | 0.6 |
| 5 | 149 | 163 | 0.6 |
| 6 | 143/139 | 163/159 | 0.6 |
| 7 | 135 | 202 | 0.6 |

The resulting product has the structure:

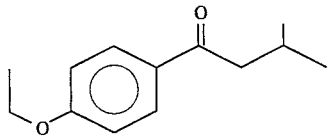

as confirmed by NMR, IR and mass spectral analyses.

EXAMPLE III(B)

Reaction:

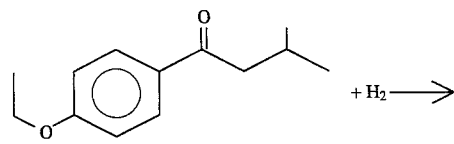

-continued
Reaction:

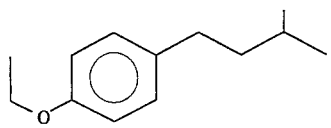

Into 1 liter autoclave equipped with hydrogen feed line are placed the following ingredients:

438 grams of the compound having the structure:

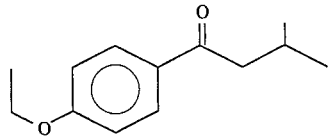

prepared according to Example III(A);

85 grams anhydrous isopropyl alcohol; and 4 grams 1% palladium on carbon.

The autoclave is sealed and the contents are heated to 110°–115° C. Hydrogen is fed in keeping the pressure at 400 psig. The hydrogen feed continues for a period of 2.25 hours maintaining the pressure at 400 psig and maintaining the temperature in the range of 115°–128° C. At the end of the 2.25 hour period, the autoclave is cooled, depressurized and opened. The resulting mixture is filtered. The filtrate is then fractionally distilled yielding the following fractions:

| Fraction Number | Vapor Temperature (°C.) | Liquid Temperature (°C.) | Vacuum mm/Hg Pressure |
|---|---|---|---|
| 1 | 23/82 | 23/114 | 150/1 |
| 2 | 86 | 114 | 1 |
| 3 | 87 | 114 | 1 |
| 4 | 89 | 115 | 1 |
| 5 | 91 | 118 | 1 |
| 6 | 93 | 116 | 1 |
| 7 | 96 | 120 | 1.5 |
| 8 | 91 | 116 | 1.0 |
| 9 | 91 | 116 | 1.0 |
| 10 | 90 | 116 | 1.0 |
| 11 | 90 | 116 | 1.2 |
| 12 | 90 | 116 | 1.0 |
| 13 | 89 | 116 | 1.0 |
| 14 | 89 | 116 | 1.0 |
| 15 | 45 | 135 | 1.0 |
| 16 | 30 | 200 | 0.5 |

Fractions 6–12 are bulked. The resulting product of which Fractions 6–12 consists has the structure:

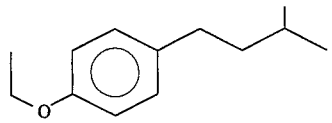

EXAMPLE III(C)

Reaction:

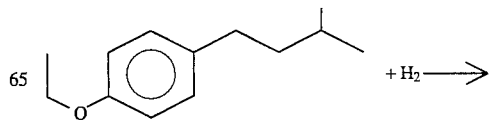

-continued
Reaction:

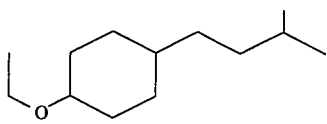

Into a 1 liter autoclave equipped with hydrogen feed line are placed the following ingredients:

200 grams (1.1 moles) of the compound having the structure:

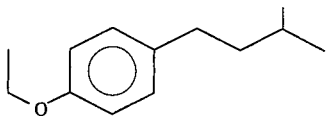

prepared according to Example III(B);
150 grams anhydrous isopropyl alcohol; and
11.2 grams of 3% ruthenium on carbon.

The autoclave is sealed and the contents are heated to 115°–120° C. The autoclave is pressurized at 400 psig with hydrogen and maintained at a temperature of 115°–120° C. at 400 psig hydrogen for a period of 2.5 hours. At the end of the 2.5 hour period, the autoclave is cooled and opened and the contents are filtered. The resulting filtrate is fractionally distilled on a fractional distillation column yielding the following fractions:

| Fraction Number | Vapor Temperature (°C.) | Liquid Temperature (°C.) | Vacuum mm/Hg Pressure |
| --- | --- | --- | --- |
| 1 | 23/33 | 23/100 | 150/60 |
| 2 | 90 | 102 | 2 |
| 3 | 92 | 100 | 2 |
| 4 | 92 | 100 | 2 |
| 5 | 89 | 97 | 1 |
| 6 | 87 | 98 | 1 |
| 7 | 85 | 100 | 0.6 |
| 8 | 81 | 101 | 0.6 |
| 9 | 82 | 104 | 0.5 |

Fractions 5–8 are bulked. Fractions 5–8 consist of the compound having the structure:

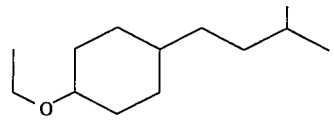

contains 85% of the isomer having the structure:

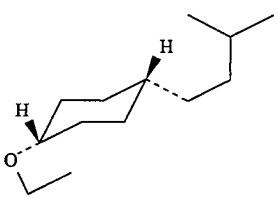

and 15% by weight of the isomer having the structure:

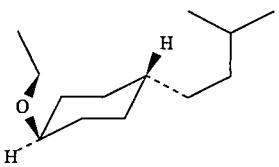

("CIS":"TRANS"). The structures were confirmed by mass spectral, NMR and IR analyses.

EXAMPLE IV

PERFUME FORMULATIONS

The following woody cologne perfume formulations are prepared:

| Ingredients | Parts by Weight | | | |
| --- | --- | --- | --- | --- |
|  | IV(A) | IV(B) | IV(C) | IV(D) |
| Bergamot oil | 150 | 150 | 150 | 150 |
| Orange oil | 200 | 200 | 200 | 200 |
| Lemon oil | 50 | 50 | 50 | 50 |
| Eugenol | 10 | 10 | 10 | 10 |
| 4-(4-methyl-4-hydroxy amyl-Δ³-cyclohexene) carboxaldehyde (LYRAL ® Trademark of International Flavors & Fragrances Inc. of New York, New York) | 40 | 40 | 40 | 40 |
| Ylang oil | 2 | 2 | 2 | 2 |
| Petitgrain Paraguay | 10 | 10 | 10 | 10 |
| γ-Methyl ionone | 20 | 20 | 20 | 20 |
| Vetiver Venezuela | 18 | 18 | 18 | 18 |
| 3-α-Methyl-dodecahydro-6,6,9a-trimethylnaptho[2,1-b]furan | 5 | 5 | 5 | 5 |
| Product produced by the reaction of acetic anhydride, polyphosphoric acid and 1,5,9-trimethyl cyclododecatriene-1,5,9 according to the process of Example I of U.S. Letters Patent | 50 | 50 | 50 | 50 |

|  | Parts by Weight | | | |
|---|---|---|---|---|
| Ingredients | IV(A) | IV(B) | IV(C) | IV(D) |
| No. 3,718,697, the specification for which is incorporated by reference herein. | | | | |
| Octahydro-9,9-dimethyl-1,6-methanonaphthalene-1-[2H]-ol produced according to Example III of U.S. Letters Patent No. 3,996,169, the specification for which is incorporated by reference herein. | 50 | 50 | 50 | 50 |
| The compound having the structure: 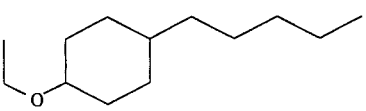 produced according to Example I(C), distillation fraction No. 8. | 12 | 0 | 0 | 0 |
| The compound having the structure: 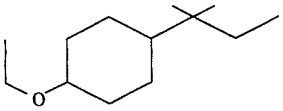 produced according to Example II(B), bulked distillation fractions Nos. 6–14. | 0 | 12 | 0 | 0 |
| The compound having the structure: 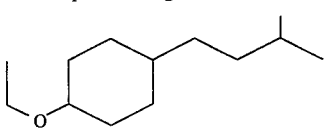 produced according to Example III(C), bulked distillation fractions Nos. 5–8. | 0 | 0 | 12 | 0 |
| The 30:30:40 (weight:weight:weight) mixture of compounds having the structures: 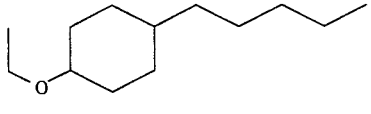 ; 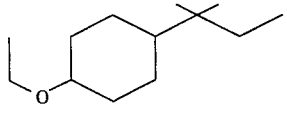 ; and 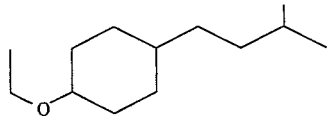 produced respectively, according to Examples I(C), II(B) and III(C). | 0 | 0 | 0 | 12 |

The compound having the structure:

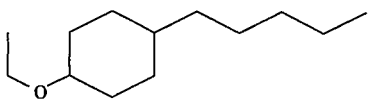

imparts to this "woody cologne" formulation green, citrus, ozoney, privet hedge (*Ligustrum vulgare*)-like undertones. Accordingly, the perfume of Example IV(A) can be described as having:

a woody cologne aroma with green, citrus, ozoney, privet hedge (*Ligustrum vulgare*)-like undertones.

The compound having the structure:

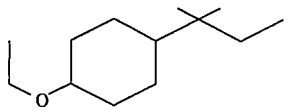

imparts to this woody cologne formulation green (fresh cut grass-like), woody, floral (muguet), balsamic, linden blossom, cucumber and melon-like undertones and green, ozoney, woody, floral (muguet) topnotes. Accordingly, the perfume composition of Example IV(B) can be described as having:

a woody cologne aroma with green (fresh cut grass-like), woody, floral (muguet), balsamic, linden blossom, cucumber and melon-like undertones with green, ozoney, woody and floral (muguet) topnotes.

The compound having the structure:

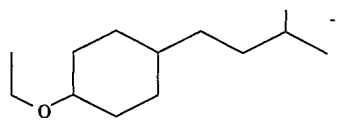

imparts to this woody cologne formulation floral (rose petal), tomato leaf, green and muguet undertones with powdery, floral (rose), green, muguet, robusta coffee, dark cocoa, fruity, tomato leaf and fatty-oily topnotes. Accordingly, the perfume formulation of Example IV(C) can be described as having:

a woody cologne aroma with floral (rose petal), tomato leaf, green, muguet undertones and powdery, floral (rose), green, muguet, robusta coffee, dark cocoa, fruity, tomato leaf and fatty-oily topnotes.

The mixture of compounds (30:30:40) having the structures:

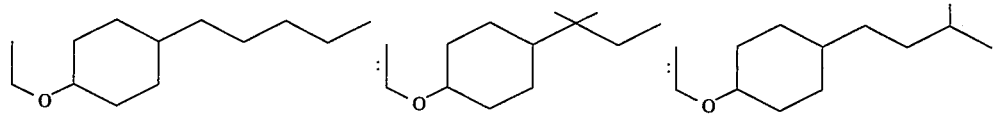

can be described as having:

a woody cologne aroma with green, fresh cut grass-like, citrus, ozoney, privet hedge (*Ligustrum vulgare*)-like, woody, floral, muguet, rose petal, balsamic, tomato leaf, linden blossom, cucumber and melon-like undertones with green, ozoney, woody, floral, muguet, rose, powdery, robusta coffee, dark cocoa, fruity, fatty-oily and tomato leaf topnotes.

EXAMPLE V

PREPARATION OF COSMETIC POWDER COMPOSITION

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure:<br />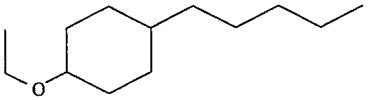<br />prepared according to Example I(C), distillation fraction No. 8. | A green, citrus, ozoney, privet hedge (*Ligustrum vulgare*)-like aroma. |
| The compound having the structure:<br />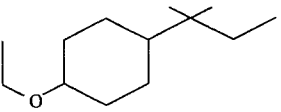<br />prepared according to Example II(B), bulked distillation fractions 6–14. | A green (fresh cut grass-like), woody, floral (muguet), balsamic aroma with green, ozoney, woody, floral (muguet) topnotes and linden blossom, cucumber and melon-like undertones. |
| The compound having the structure:<br />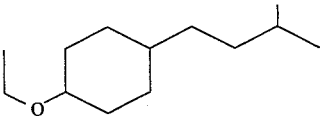<br />prepared according to Example III(C), bulked distillation fractions 5–8. | A floral (rose petal), tomato leaf, green, muguet aroma with powdery, floral (rose), green, muguet, robusta coffee, dark cocoa, fruity, tomato leaf and fatty-oily topnotes. |
| Perfume composition of Example IV(A). | A woody cologne aroma with green, citrus, ozoney, privet hedge (*Ligustrum vulgare*)-like undertones. |
| Perfume composition of Example IV(B). | A woody cologne aroma with green (fresh cut grass-like), woody, floral (muguet), balsamic, linden blossom, cucumber and melon-like undertones with green, ozoney woody and floral (muguet) topnotes. |
| Perfume composition of Example IV(C). | A woody cologne aroma with floral (rose petal), tomato leaf, green muguet undertones and powdery, floral (rose), green, muguet, robusta coffee, dark cocoa, fruity, tomato leaf and fatty-oily topnotes. |
| Perfume composition of Example IV(D) | A woody cologne aroma with green, fresh cut grass-like, citrus, ozoney, privet hedge (*Ligustrum vulgare*)-like, woody, floral, muguet, rose petal, balsamic, tomato leaf, linden blossom, cucumber and melon-like undertones with green, ozoney, woody, floral, muguet, rose, powdery, robusta coffee, dark cocoa, fruity, fatty-oily and tomato leaf topnotes. |

EXAMPLE VI

PERFUMED LIQUID DETERGENTS

Concentrated liquid detergents (lysine salt of n-dodecylbenzene sulfonic acid as more specifically described in U.S. Pat. No. 3,948,818 issued Apr. 6, 1976 and incorporated by reference herein) with aroma nuances as set forth in Table II of Example V are prepared containing 0.10%, 0.15%, 0.20%, 0.30% and 0.35% of the substance set forth in Table II of Example V. They are prepared by adding and homogeneously mixing the appropriate quantity of substance set forth in Table II of Example V in the liquid detergent. The detergents all possess excellent aromas as set forth in Table II of Example V, the intensity increasing with greater concentrations of substances as set forth in Table II of Example V.

EXAMPLE VII

PREPARATIONS OF COLOGNES AND HANDKERCHIEF PERFUMES

Compositions as set forth in Table II of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example V are imparted to the colognes and to the handkerchief perfumes at all levels indicated.

EXAMPLE VIII

PREPARATION OF SOAP COMPOSITIONS

100 Grams of soap chips [per sample] (IVORY®, produced by the Procter & Gamble Company of Cincinnati, Ohio) are each mixed with 1 gram samples of substances as set forth in Table II of Example V until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table II of Example V.

EXAMPLE IX

PREPARATION OF SOLID DETERGENT COMPOSITIONS

Detergents are prepared using the following ingredients according to Example I of Canadian Patent No. 1,007,948 (incorporated by reference herein):

| Ingredient | Percent by Weight |
|---|---|
| NEODOL ® 45-11 (a $C_{12}$–$C_{15}$ alcohol ethoxylated with 11 moles of ethylene oxide) | 12 |
| Sodium carbonate | 55 |
| Sodium citrate | 20 |
| Sodium sulfate, water-brighteners | q.s. |

This detergent is a phosphate-free detergent. Samples of 100 grams each of this detergent are admixed with 0.10, 0.15, 0.20 and 0.25 grams of each of the substances as set forth in Table II of Example V. Each of the detergent samples has an excellent aroma as indicated in Table II of Example V.

EXAMPLE X

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:

1. A water "dissolvable" paper ("Dissolvo Paper");

2. Adogen 448 (m.p. about 140° F.) as the substrate coating; and

3. An outer coating having the following formulation (m.p. about 150° F.):

57% $C_{20\text{-}22}$ HAPS;
22% isopropyl alcohol;
20% antistatic agent; and
1% of one of the substances as set forth in Table II of Example V.

Fabric softening compositions prepared according to Example I at column 15 of U.S. Pat. No. 3,632,396 having the aroma characteristics as set forth in Table II of Example V, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example V is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example V, supra.

EXAMPLE XI

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% of food grade ethanol. 8.0 Grams of the polymer is dissolved in the alcohol. The following ingredients are added to the PVP/VA alcoholic solution:

| Ingredient | Percent by Weight |
|---|---|
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table II of Example V, supra | 0.10 |

The perfuming substances as set forth in Table II of Example V add aroma characteristics as set forth in Table II of Example V which are rather intense and aesthetically pleasing to the users of the soft-feel, good-hold pump hair sprays.

EXAMPLE XII

CONDITIONING SHAMPOOS

Monamid CMA (prepared by the Mona Industries Company) (3.0 weight percent) is melted with 2.0 weight percent coconut fatty acid (prepared by the Procter & Gamble Company of Cincinnati, Ohio; 1.0 weight percent ethylene glycol distearate (prepared by the Armak Corporation) and triethanolamine (a product of the Union Carbide Corporation) (35.0 weight percent). The resulting mixture is heated to 60° C. and mixed until a clear solution is obtained (at 60° C.). This material is "COMPOSITION A".

GAFQUAT® 755N polymer (manufactured by the GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation. This material is "COMPOSITION B".

The resulting "COMPOSITION A" and "COMPOSITION B" are than mixed in a 50:50 weight ratio of A:B and cooled to 45° C. and 0.3 weight percent of perfuming substance as set forth in Table II of Example V is added to the mixture. The resulting mixture is cooled to 40° C. and blending is carried out for an additional one hour in each case. At the end of this blending period, the resulting material has a pleasant fragrance as indicated in Table II of Example V.

What is claimed is:

1. A process for preparing at least one compound defined according to the structure:

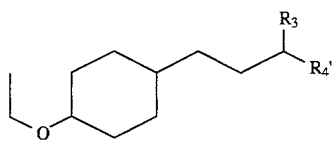

comprising the steps of:
(i) carrying out the reaction:

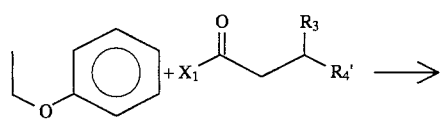

in the presence of a Lewis acid catalyst; then
(ii) carrying out the reaction:

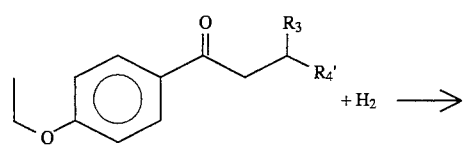

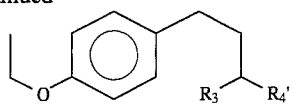

in the presence of a hydrogenation catalyst; and then
(iii) carrying out the reaction:

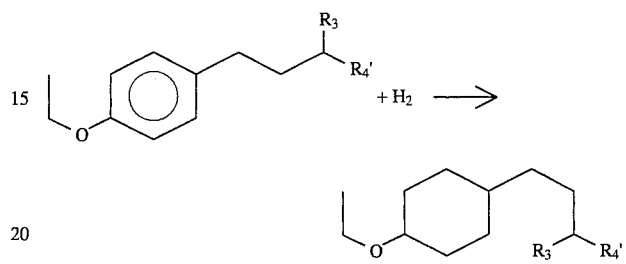

in the presence of a ruthenium on carbon catalyst wherein $X_1$ represents chloro, bromo or hydroxyl; wherein $R_4'$ represents ethyl or methyl; and wherein $R_3$ represents hydrogen or methyl with the proviso that the sum of the carbon atoms in $R_3$ and $R_4'$ is 2.

2. A process for producing a compound defined according to the structure:

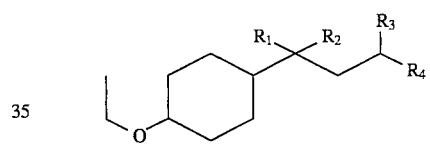

comprising the step of reacting an alkyl phenol defined according to the structure:

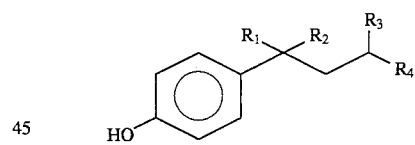

with a base defined according to the structure:

according to the reaction:

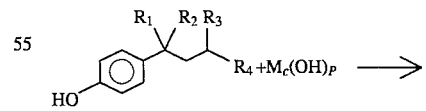

-continued

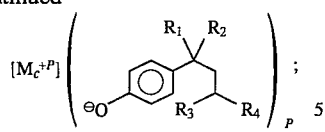

then carrying out an ethoxylation reaction according to the reaction:

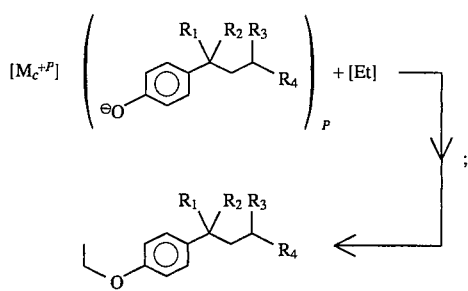

and then carrying out a hydrogenation reaction according to the reaction:

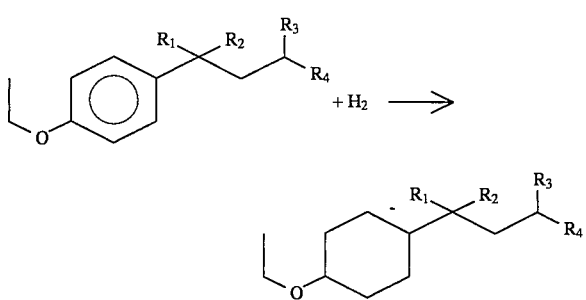

wherein $R_1$, $R_2$ and $R_3$ represent the same or different methyl or hydrogen; and wherein $R_4$ represents hydrogen, methyl or ethyl with the proviso that the sum of the number of carbon atoms in $R_1$, $R_2$, $R_3$ and $R_4$ is 2; wherein $M_C$ represents alkali metal or alkaline earth metal; wherein P is an integer selected from the group consisting of 1 and 2; wherein the symbol:

[εt]

represents an ethoxylation reagent; and wherein the reaction:

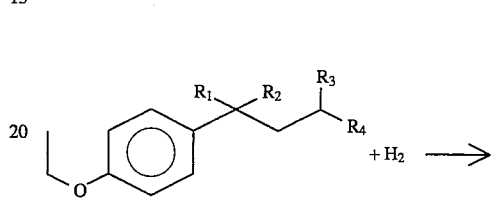

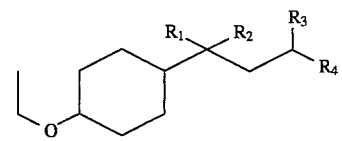

is carried out using a ruthenium on carbon catalyst.

* * * * *